US011442057B2

(12) United States Patent
Kim et al.

(10) Patent No.: US 11,442,057 B2
(45) Date of Patent: Sep. 13, 2022

(54) METHOD FOR SCREENING ANTICANCER AGENT INHIBITING BINDING OF AIMP2-DX2 AND HSP70

(71) Applicant: MEDICINAL BIOCONVERGENCE RESEARCH CENTER, Suwon-si (KR)

(72) Inventors: Sunghoon Kim, Seoul (KR); Dae Gyu Kim, Seoul (KR); Semi Lim, Seoul (KR)

(73) Assignee: MEDICINAL BIOCONVERGENCE RESEARCH CENTER, Suwon-si (KR)

(*) Notice: Subject to any disclaimer, the term of this patent is extended or adjusted under 35 U.S.C. 154(b) by 543 days.

(21) Appl. No.: 16/125,113

(22) Filed: Sep. 7, 2018

(65) Prior Publication Data

US 2019/0033295 A1 Jan. 31, 2019

Related U.S. Application Data

(63) Continuation of application No. PCT/KR2017/002442, filed on Mar. 7, 2017.

(30) Foreign Application Priority Data

Mar. 7, 2016 (KR) .................. 10-2016-0027077

(51) Int. Cl.
*G01N 33/68* (2006.01)
*C12Q 1/02* (2006.01)
*C12Q 1/25* (2006.01)
*G01N 33/50* (2006.01)
*G01N 33/574* (2006.01)
*A61K 31/5377* (2006.01)
*A61K 48/00* (2006.01)
*A61K 31/404* (2006.01)

(52) U.S. Cl.
CPC ........ *G01N 33/5011* (2013.01); *A61K 31/404* (2013.01); *A61K 31/5377* (2013.01); *A61K 48/00* (2013.01); *G01N 33/50* (2013.01); *G01N 33/574* (2013.01); *G01N 2500/02* (2013.01)

(58) Field of Classification Search
CPC .................................................. G01N 33/68
See application file for complete search history.

(56) References Cited

U.S. PATENT DOCUMENTS

2006/0115832 A1* 6/2006 Hoon .................. C12Q 1/6886
435/6.16
2006/0275844 A1* 12/2006 Linke ..................... G16H 70/60
435/7.23
2008/0280297 A1* 11/2008 Dalla-Favera ..... C07K 16/3061
435/6.16
2011/0117572 A1 5/2011 Kim et al.
2012/0178111 A1* 7/2012 Diamandis ....... G01N 33/57423
435/7.92

FOREIGN PATENT DOCUMENTS

| KR | 10-0762995 B1 | 10/2007 |
| KR | 10-2009-0048382 A | 5/2009 |
| KR | 10-2014-0145895 A | 12/2014 |
| KR | 10-1577315 B1 | 12/2015 |

OTHER PUBLICATIONS

Baxevanis (Expert Opinion: Drug Discovery, vol. 3, No. 4, p. 441-452, 2008) (Year: 2008).*
Burgess et al. (J of Cell Bio. 111:2129-2138, 1990) (Year: 1990).*
Lazar et al. (Molecular and Cellular Biology 8:1247-1252, 1988) (Year: 1988).*
Ju (Proceedings of the National Academy of Sciences, U.S.A., vol. 88, p. 2658-2662, 1991) (Year: 1991).*
Baker (Immunity, vol. 13, p. 475-484, 2000) (Year: 2000).*
Huang (The Journal of Biological Chemistry, vol. 272, No. 43, p. 27155-27159, 1997) (Year: 1997).*
Martindale (Nature Genetics, vol. 18, p. 150-154, 1998) (Year: 1998).*
Nonaka (Human Molecular Genetics, vol. 18, No. 18, p. 3353-3364, 2009) (Year: 2009).*
Choi et al., "Splicing variant of AIMP2 as an effective target against chemoresistant ovarian cancer," Journal of Molecular Cell Biology, vol. 4, No. 3, pp. 164-173 (2012).
International Search Report corresponding to Korean Patent Application Serial No. PCT/KR2017/002442 dated Jun. 16, 2017.
Bruns AF et al, PloS one, 7:e48539, 2012.
Calderwood SK et al, "Heat shock proteins in cancer: chaperones of tumorigenesis," Trends in Biochemical Sciences, vol. 31, pp. 164-172 (2006).
Eustace BK et al, "Functional proteomic screens reveal an essential extracellular role for hsp90 alpha in cancer cell invasiveness." Nature cell biology, vol. 6, pp. 507-514, (2004).
Eustace BK et al, "Extracellular roles for the molecular chaperone, hsp90." Cell cycle, vol. 3, pp. 1098-1100, (2004).

(Continued)

*Primary Examiner* — Michael Allen
(74) *Attorney, Agent, or Firm* — Jenkins, Wilson, Taylor & Hunt, P.A.

(57) ABSTRACT

The present invention relates to a method for screening an anticancer agent which inhibits the binding of AIMP2-DX2 and HSP70. In addition, the pharmaceutical composition for preventing or treating cancer comprising, as an active ingredient, an anticancer agent screened according to the method of the present invention inhibits the expression of HSP70 or inhibits the binding of HSP70 and AIMP2-DX2, thereby lowering the level of AIMP2-DX2 protein, and can effectively prevent the progression of cancer. As such, the pharmaceutical composition can be useful for developing a cancer treating agent.

5 Claims, 21 Drawing Sheets
(14 of 21 Drawing Sheet(s) Filed in Color)
Specification includes a Sequence Listing.

(56) References Cited

OTHER PUBLICATIONS

Gong et al., "Invastion potential of H22 hepatocarcinoma cells is increased by HMGB1-induced tumor NF-kB signaling via initiation of HSP70", Oncology Reports, vol. 30: pp. 1249-1256, (2013).

International Preliminary Report on Patentability Corresponding to International Application No. PCT/KR 2017/002442 dated Sep. 11, 2018.

Jaattela M, "Over-expression of hsp70 confers tumorigenicity to mouse fibrosarcoma cells." International journal of cancer, vol. 60, pp. 689-693, (1995).

Morano KA, "New tricks for an old dog: The evolving world of Hsp70." Annals of the New York Academy of Sciences, vol. 1113, pp. 1-14, (2007).

Murphy ME, "The HSP70 family and cancer." Carcinogenesis, vol. 34(6), pp. 1181-1188, (2013).

Seo JS et al, "T Cell Lymphoma in Transgenic Mice Expressing the HumanHsp70Gene." Biochemical and biophysical research communications, vol. 218(2), pp. 582-587, (1996).

Sun J et al, "Induction of Angiogenesis by Heat Shock Protein 90 Mediated by Protein Kinase Akt and Endothelial Nitric Oxide Synthase." Arteriosclerosis, thrombosis and vascular biology. vol. 24(12), pp. 2238-2244, (2004).

Volloch VZ et al, "Oncogenic potential of Hsp72." Oncogene, vol. 18, pp. 3648-3651, (1999).

English Translation of the Written Opinion of the International Searching Authority Corresponding to International Application No. PCT/KR 2017/002442 dated Jun. 15, 2017.

Zhou J et al, "PI3K/Akt Is Required for Heat Shock Proteins to Protect Hypoxia-inducible Factor 1α from pVHL-independent Degradation." The Journal of biological chemistry, vol. 279, pp. 13506-13513, (2004).

\* cited by examiner

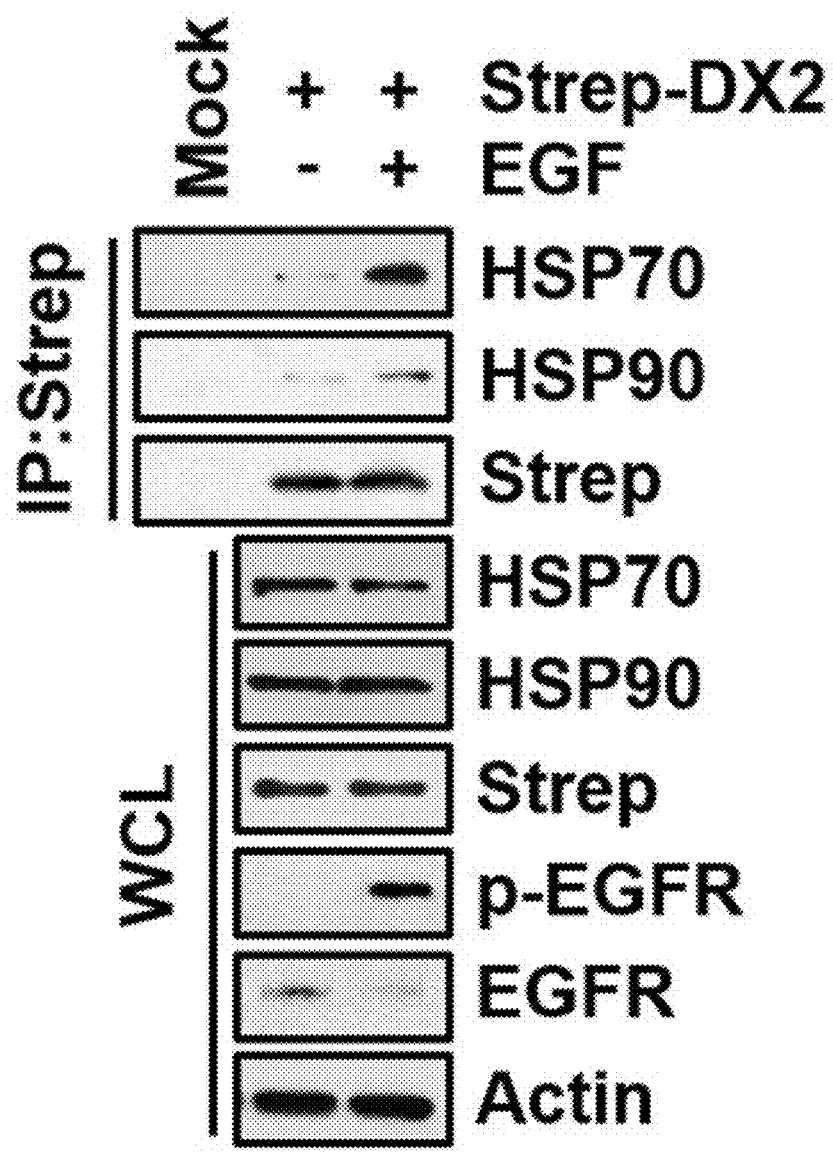

| $K_a$ (1/Ms) | $K_d$ (1/s) | $K_D$ (M) |
|---|---|---|
| $1.03 \times 10^6$ | $4.93 \times 10^{-4}$ | $4.79 \times 10^{-10}$ |

BC-DXI-495

| Expression | Cell line | GI$_{50}$ |
|---|---|---|
| Low | WI-26 | 100 |
| | WI-38 | 100 |
| | NCI-H2087 | 100 |
| Median | HCC-1359 | 100 |
| | HCC-95 | 71.66 |
| | HCC-366 | 61.12 |
| High | HCC-1438 | 38.59 |
| | HCC-1588 | 27.38 |
| | NCI-H460 | 20.49 |

METHOD FOR SCREENING ANTICANCER AGENT INHIBITING BINDING OF AIMP2-DX2 AND HSP70

RELATED APPLICATIONS

This is a continuation of International Application PCT/KR2017/002442, with an international filing date of Mar. 7, 2017, the disclosure of which is incorporated herein by reference in its entirety, and which claims priority from Korean Patent Application No. 10-2016-0027077, filed on Mar. 7, 2016, the entire contents of which are incorporated herein by reference.

TECHNICAL FIELD

The present invention relates to a method for screening an anti-cancer agent which inhibits the binding of AIMP2-DX2 and HSP70. More specifically, the present invention relates to a method for screening an anti-cancer agent, the method comprising the steps of: (a) contacting AIMP2-DX2 or a fragment thereof with HSP70 or a fragment thereof in the presence or absence of a test substance; (b) measuring a binding level of AIMP2-DX2 and HSP70 in the presence or absence of the test substance; (c) comparing the binding level of AIMP2-DX2 with HSP70 in the presence of the test substance with the binding level of AIMP2-DX2 with HSP70 in the absence of the test substance to determine a change in the binding level of AIMP2-DX2 and HSP70 by the test substance; (d) selecting the test substance that reduces the binding level of AIMP2-DX2 and HSP70; and (e) verifying the anti-cancer activity of the selected test substance in cells or animals, together with an anti-cancer composition comprising an anti-cancer agent selected by the method, as an active ingredient.

BACKGROUND OF THE INVENTION

Development of cancer-specific markers is required not only for diagnosis of cancer, but also for cancer-specific treatment. Cytotoxic therapies have been used extensively in cancer therapy for more than 50 years since it was first used as an anti-cancer agent. However, in addition to cancer cells, they act nonspecifically on cells of other organs whose division rate is comparatively fast, exhibit strong toxicity, and causing serious side effects. In order to overcome the side effects and tolerance of such existing anti-cancer agents, studies have been conducted to develop therapeutic agents that act specifically on tumor cells using cancer specific markers that appear in the normal cell carcinogenesis process. The key to emerging cancer-targeted therapies to minimize toxicity by anti-cancer agents is to find cancer-specific genes.

Meanwhile, Heat Shock Protein (HSP) is a molecular chaperone that plays a key role in maintaining protein homeostasis. HSP is important for cell survival in stress situations such as hypoxia. HSPs, particularly HSP90 and HSP70, are highly expressed in a wide range of tumors [Morano K A, Annals of the New York Academy of Sciences, 1113:1-14, 2007; Calderwood S K et al, Trends in biochemical sciences, 31:164-72, 2006]. Expression of some HSPs has been shown to correlate with proliferation, differentiation, and apoptosis of tumor cells in some cancers, showing that HSP plays an important role in cancer cell survival because of its own cell protection role. It has been reported that overexpression of HSP70 causes tumorigenesis in mouse fibrosarcoma cells, while the overexpression of HSP70 in T-cells of transgenic mice causes an increase in T-cell lymphoma of the mice [Jaattela M, International journal of cancer Journal international du cancer, 60:689-93, 1995; Seo J S et al, Biochemical and biophysical research communications, 218:582-7, 1996; Volloch V Z et al, Oncogene, 18:3648-51, 1999; Murphy M E, Carcinogenesis, 34:1181-8, 2013]. In particular, HSP70 is known to play an important role in protecting cells from apoptosis. Furthermore, the increased expression of HSP is known to be involved in angiogenesis, invasion, and metastasis [Calderwood S K et al, Trends in biochemical sciences, 31:164-72. 2006; Zhou J et al, The Journal of biological chemistry, 279: 13506-13, 2004; Bruns A F et al, PloS one, 7:e48539, 2012; Sun J et al, Arteriosclerosis, thrombosis and vascular biology. 24:2238-44, 2004; Gong W, et al, Oncology reports, 2013; Eustace B K et al, Cell cycle, 3:1098-100, 2004; Eustace B K et al, Nature cell biology, 6:507-14, 2004].

AIMP2 (aminoacyl-tRNA synthetase complex-interacting multifunctional protein 2) is one of the proteins involved in the formation of the aminoacyl-tRNA synthetase (ARS) complex, which is also called p38/JTV-1 or p38. AIMP2 is known as a novel tumor suppressor to have a function of enhancing TGF-beta signaling through direct interaction with Smad2/3. It is known that AIMP2-DX2, an exon 2-deficient variant form of AIMP2, is specifically expressed in cancer cell lines and tissues (Korean Patent No. 10-0762995).

As described above, it is known that AIMP2-DX2 and HSP70 are associated with differentiation or survival of tumor cells, but it is not known how their correlation is related to cancer.

DETAILED DESCRIPTION OF THE INVENTION

Technical Problem

Accordingly, the inventors of the present invention studied the interaction between AIMP2-DX2 and HSP70 and found that HSP70 directly binds to AIMP2-DX2 to stabilize AIMP2-DX2 protein and consequently play a crucial role in the survival and differentiation of cancer cells. Therefore, the present invention has been completed in view of the findings that the inhibition of the binding of HSP70 to AIMP2-DX2 can inhibit cell division and proliferation.

Accordingly, an aspect of the present invention is to provide a method for screening an anti-cancer agent, the method comprising the steps of:

(a) contacting AIMP2-DX2 or a fragment thereof with HSP70 or a fragment thereof in the presence or absence of a test substance;

(b) measuring a binding level of AIMP2-DX2 and HSP70 in the presence or absence of the test substance;

(c) comparing the binding level of AIMP2-DX2 with HSP70 in the presence of the test substance with the binding level of AIMP2-DX2 with HSP70 in the absence of the test substance to determine a change in the binding level of AIMP2-DX2 and HSP70 by the test substance;

(d) selecting the test substance that reduces the binding level of AIMP2-DX2 and HSP70; and (e) verifying the anti-cancer activity of the selected test substance in cells or animals.

Another aspect of the present invention is to provide a composition for preventing or treating cancer comprising an anti-cancer agent selected by the screening method, as an active ingredient.

Also, another aspect of the present invention is to provide a composition for preventing or treating cancer consisting of an anti-cancer agent selected by the screening method, as an active ingredient.

Also, another aspect of the present invention is to provide a composition for preventing or treating cancer consisting essentially of an anti-cancer agent selected by the screening method, as an active ingredient.

Another aspect of the present invention is to provide use of an anti-cancer agent selected by the screening method for the preparation of an agent for preventing or treating a cancer.

Still another aspect of the present invention is to provide a method for preventing or treating a cancer in a subject, the method comprising administering an effective amount of an anti-cancer agent selected by the screening method to a subject in need thereof.

Technical Solution

An embodiment according to an aspect of the present invention provides a method for screening an anti-cancer agent, the method comprising the steps of:

(a) contacting AIMP2-DX2 or a fragment thereof with HSP70 or a fragment thereof in the presence or absence of a test substance;

(b) measuring a binding level of AIMP2-DX2 and HSP70 in the presence or absence of the test substance;

(c) comparing the binding level of AIMP2-DX2 with HSP70 in the presence of the test substance with the binding level of AIMP2-DX2 with HSP70 in the absence of the test substance to determine a change in the binding level of AIMP2-DX2 and HSP70 by the test substance;

(d) selecting the test substance that reduces the binding level of AIMP2-DX2 and HSP70; and (e) verifying the anti-cancer activity of the selected test substance in cells or animals.

An embodiment according to another aspect of the present invention provides a composition for preventing or treating cancer comprising an anti-cancer agent selected by the screening method, as an active ingredient.

Also, an embodiment according to another aspect of the present invention provides a composition for preventing or treating cancer consisting of an anti-cancer agent selected by the screening method, as an active ingredient.

Alto, an embodiment according to another aspect of the present invention provides a composition for preventing or treating cancer consisting essentially of an anti-cancer agent selected by the screening method, as an active ingredient.

An embodiment according to another aspect of the present invention provides use of an anti-cancer agent selected by the screening method for the preparation of an agent for preventing or treating a cancer.

An embodiment according to another aspect of the present invention provides a method for treating a cancer in a subject, the method comprising administering an effective amount of an anti-cancer agent selected by the screening method to a subject in need thereof.

Hereinafter, the present invention will be described in detail.

The present invention provides a method for screening an anti-cancer agent, the method comprising the steps of:

(a) contacting AIMP2-DX2 or a fragment thereof with HSP70 or a fragment thereof in the presence or absence of a test substance;

(b) measuring a binding level of AIMP2-DX2 and HSP70 in the presence or absence of the test substance;

(c) comparing the binding level of AIMP2-DX2 with HSP70 in the presence of the test substance with the binding level of AIMP2-DX2 with HSP70 in the absence of the test substance to determine a change in the binding level of AIMP2-DX2 and HSP70 by the test substance;

(d) selecting the test substance that reduces the binding level of AIMP2-DX2 and HSP70; and (e) verifying the anti-cancer activity of the selected test substance in cells or animals.

The present inventors have found that, in addition to the original function of HSP70, the HSP70 protein binds to AIMP2-DX2 to stabilize the AIMP2-DX2 protein from degradation, and promotes the differentiation and growth of tumor cells due to AIMP2-DX2. Factors capable of inhibiting the expression of HSP70 to reduce the level of HSP70 that can react with AIMP2-DX2, or directly inhibiting the reaction of HSP70 with AIMP2-DX2 reduce AIMP2-DX2 protein levels, resulting in the inhibition of tumor cell growth and differentiation. Based on the findings of the functional relationship between HSP70 and AIMP2-DX2, the present inventors disclosed herein for the first time the anti-cancer agent screening method of screening have screened an agent capable of inhibiting the binding of HSP70 and AIMP2-DX2 to select an anti-cancer agent.

Step (a) of the method according to the present invention is a step of contacting AIMP2-DX2 or a fragment thereof with HSP70 or a fragment thereof in the presence or absence of a test substance.

As used herein, the term 'protein' is used interchangeably with 'polypeptide' or 'peptide' and for example, refers to a polymer of amino acid residues as commonly found in naturally occurring proteins. The term 'fragment' means a portion of a protein. The term 'polynucleotide' or 'nucleic acid' refers to deoxyribonucleotide (DNA) or ribonucleotide (RNA) in the form of single strand or double strands. Unless otherwise limited, it also includes known analogs of natural nucleotides that hybridize to nucleic acids in a manner similar to naturally occurring nucleotides. The term 'mRNA' is a RNA that transfers genetic information (gene-specific nucleotide sequence) to ribosomes that specify amino acid sequences from a specific gene during protein synthesis.

In the present invention, the term "AIMP2-DX2" is a mutant in which the region of Exon 2 is deleted in AIMP2 protein sequence (312aa version: AAC50391.1 or GI:1215669; 320aa version: AAH13630.1, GI:15489023, BC013630.1), and includes a protein in which the region of exon 2 is deleted in the AIMP2 equivalent (functional equivalents having substantially equivalent activity to AIMP2 as variants of amino acid sequence substitutions, deletions, insertions, or combinations thereof, or functional derivatives that have a modification leading to increase or decrease physicochemical properties but have a substantially equivalent activity to AIMP2). As used herein, the term "deletion of the region of Exon 2" in the AIMP2 protein sequence indicates that a mutant in which the amino acid sequence of the exon 2 region is partially or totally lost in the AIMP2 protein forms a heterodimer with the AIMP2 protein, resulting in the interference with the normal function of the AIMP2 protein. Thus, the AIMP2-DX2 as used herein includes these in which the entire amino acid sequences of Exon2 or a portion these of are deleted, together with these in which a portion of Exon 1, Exon 3 and/or Exon 4 region is further deleted.

The AIMP2-DX2 protein for carrying out the method of the present invention may preferably be derived from mammals, including humans. Most preferably, the AIMP2-DX2 protein may comprise a human AIMP2-DX2 protein amino acid sequence of SEQ ID NO: 1.

Also, the fragment of AIMP2-DX2 means a fragment comprising a part of AIMP2-DX2 necessary for its binding to HSP70. The inventors have confirmed that the DX2 portion of the AIMP2-DX2 protein, not the AIMP2 portion, binds to HSP70. Therefore, the fragment of AIMP2-DX2 for carrying out the present invention preferably comprises amino acid residues 1 to 87 of the human AIMP2-DX2 amino acid sequence of SEQ ID NO: 1, while most preferably, it may be the amino acid sequence of SEQ ID NO: 2, but is not limited thereto.

As used herein, the term 'HSP70' is a heat shock protein (HSP) 70, which is a molecular chaperone that plays a key role in maintaining protein homeostasis. HSP70 is important for cell survival in such stress situations as hypoxia. On the other hand, HSP70 is highly expressed in a wide range of tumors [Morano K A, Annals of the New York Academy of Sciences, 1113:1-14, 2007; Calderwood S K et al, Trends in biochemical sciences, 31:164-72, 2006]. Expression of HSP70 has been shown to correlate with the proliferation, differentiation, and apoptosis of tumor cells in some cancers, suggesting that HSP70 plays an important role in cancer cell survival because of its own cell protective role. It has been reported that overexpression of HSP70 causes tumorigenesis in mouse fibrosarcoma cells, while the overexpression of HSP70 in T-cells of transgenic mice causes an increase in T-cell lymphoma of the mice [Jaattela M, International journal of cancer Journal international du cancer, 60:689-93, 1995; Seo J S et al, Biochemical and biophysical research communications, 218:582-7, 1996; Volloch V Z et al, Oncogene, 18:3648-51, 1999; Murphy M E, Carcinogenesis, 34:1181-8, 2013].

The HSP70 protein for carrying out the method of the present invention may preferably be derived from mammals, including humans. Most preferably, the HSP70 protein may comprise the amino acid sequence of SEQ ID NO: 3.

Also, the fragment of HSP70 means a fragment comprising a part of HSP70 necessary for its binding to AIMP2-DX2. The present inventors confirmed that AIMP2-DX2 binds to the substrate binding domain region of HSP70. Specifically, it was revealed that a fragment containing the 385th to 536th amino acids (SEQ ID NO: 4) in the amino acid sequence of human HSP70 (SEQ ID NO: 3) can bind to AIMP2-DX2. Therefore, the fragment of HSP70 for carrying out the present invention may be a fragment comprising the amino acid sequence of the 385th to 536th amino acids (SEQ ID NO: 4) in SEQ ID NO: 3.

In addition, AIMP2-DX2 or fragments thereof, and HSP70 or fragments thereof according to the present invention include functional equivalents thereof. The term "functional equivalents" refer to a polypeptide having at least 70%, preferably at least 80%, more preferably at least 90% sequence homology (i.e, sequence identity) with the amino acid sequence of AIMP2-DX2 and a fragment thereof and HSP70 or a fragment thereof, respectively, while referring to polypeptides exhibiting substantially the homogenous physiological activity as the polypeptide of AIMP2-DX2 of SEQ ID NO: 1 and the polypeptide of HSP70 of SEQ ID NO: 3. Herein, the term 'substantially the homogenous physiological activity' means that a direct and specific binding between wild-type AIMP2-DX2 and wild-type HSP70 can be reproduced. That is, the functional equivalents of a fragment of AIMP2-DX2 mean those having an activity capable of binding to the full-length HSP70 or fragment thereof, while the functional equivalents of a fragment of HSP70 mean those having an activity capable of binding to the full-length AIMP2-DX2 or its binding sites to HSP70 AIMP2-DX2. The functional equivalents may be those resulting from the addition, substitution or deletion of some of the amino acid sequences. The substitution of the amino acid is preferably a conservative substitution. Examples of conservative substitutions of amino acids present in nature are as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur-containing amino acids (Cys, Met). The functional equivalents also include variants in which some of the amino acids are deleted in the amino acid sequence. The deletion or substitution of the amino acid is preferably located in a region where it is not directly related to the physiological activity of the polypeptides according to the present invention. Also, the deletion of the amino acid is preferably located at a site where it is not directly related to the physiological activity of the AIMP2-DX2 or HSP70 polypeptide. Also included are variants in which some amino acids are added at both ends of the amino acid sequence or within the amino acid sequence. Further, the functional equivalents herein include these polypeptide derivatives, while maintaining both the basic skeleton of the polypeptide according to the present invention and its physiological activity, in which some chemical structures of the polypeptide are modified. For example, there are included structural modifications to alter the stability, shelf stability, volatility, or solubility of the polypeptides according to the present invention.

In the methods of the present invention, the term "contacting" is a general term, and refers to the binding of two or more agents (e.g., two polypeptides) or the binding of an agent to a cell (e.g., protein and a cell). Contacting may occur in vitro. For example, two or more agents may be combined in a test tube or other container, or a test agent may be a cell or cell lysate combined with. Also, contacting may occur in cells or in situ. For example, recombinant polynucleotides encoding two polypeptides are co-expressed in a cell, thereby containing the two polypeptides in a cell or cell lysate. Also, a protein to be tested may be a protein chip or a protein array in which the protein is arranged on the surface of its stationary phase.

When the method of the present invention is carried out in a cell, AIMP2-DX2 and HSP70 are expressed intracellularly, or nucleic acids encoding AIMP2-DX2 or a fragment thereof, HSP70 or a fragment thereof are introduced into cells, respectively, and over-expressed by transfection. Also, when the method of the present invention is carried out in vitro or in situ, such as in a protein array, AIMP2-DX2 or fragments thereof and HSP70 or fragments thereof can be prepared by extraction from natural sources or by genetic engineering methods. For example, nucleic acids encoding the polypeptide or functional equivalent thereof and recombinant expression vectors may be prepared by a conventional method, and the polypeptide or functional equivalent thereof may be thereby obtained by their expressions in suitable host cells. The polypeptide required for carrying out the method of the present invention can also be produced by a chemical synthesis method known in the art.

Also, in the method of the present invention, the term 'test substance' is used interchangeably with a test agent or an agent, that includes any substance, molecule, element, compound, entity, or combination thereof. For example, it includes proteins, polypeptides, small organic molecules, polysaccharides, polynucleotides, and the like. Also, it may include natural products, synthetic compounds or chemical compounds, or combination of two or more substances.

Specifically, the anti-cancer agent selected through the method of the present invention is not limited based on its material properties as long as it can inhibit the binding of AIMP2-DX2 and HSP70, or decrease AIMP2-DX2 protein expression level capable of binding to HSP70. For example, the anti-cancer agent may include siRNA, shRNA, miRNA, ribozyme, DNAzyme, peptide nucleic acid (PNA), antisense oligonucleotide, antibody, aptamer, peptide, natural extracts and chemical substance. Preferably, the anti-cancer agent may include shRNA, siRNA, or chemical substance that can lower the expression of AIMP2-DX2, but is not limited thereto.

Step (b) of the method according to the present invention is a step of measuring a binding level of AIMP2-DX2 and HSP70 in the presence or absence of the test substance in step of (a).

In the step of measuring the binding level between AIMP2-DX2 and HSP70, any method may be used without limitation as long as it is commonly used in the art to measure the binding degree of two proteins. For example, the binding of AIMP2-DX2 and HSP70 may be measured by two-hybrid method, co-immunoprecipitation assay (co-IP), immunohistochemistry and co-localization assay, scintillation proximity assay (SPA), UV or chemical cross-linking method, bimolecular interaction analysis (BIA), mass spectrometry (MS), nuclear magnetic resonance (NMR), fluorescence polarization assays (FPA) and in vitro pull-down assay), enzyme linked immunosorbent assay (ELISA), protein chip or array, Venus biomolecular fluorescence complementation (BiFC) and so on.

In a specific example of the present invention, co-IP experiments were performed by overexpressing DX2 and HSP70 properly labeled with HA, Strep, radioactive isotope or the like in cells, or GST pull-down experiments were used to measure HSP70 protein level binding to DX2 or the DX2 protein level binding to HSP70 were measured.

Step (c) is a step of comparing the binding level of AIMP2-DX2 with HSP70 in the presence of the test substance with the binding level of AIMP2-DX2 with HSP70 in the absence of the test substance measured in step of (b) to determine a change in the binding level of AIMP2-DX2 and HSP70 by the test substance.

That is, in this step, a difference in the binding levels of AIMP2-DX2 and HSP70 proteins contacted in the presence or absence of the test substance as obtained in step (b) is evaluated, thereby determining the effect of the test substance on the binding of AIMP2-DX2 and HSP70.

Step (d) is a step of selecting the test substance that reduces the binding level of AIMP2-DX2 and HSP70.

In a specific embodiment, it was verified that AIMP2-DX2 and HSP70 are specifically bound directly in a cell, and that AIMP2-DX2 is stabilized not to be degraded through its binding with HSP70, resulting in the maintenance of cell proliferation and differentiation by AIMP2-DX2. The AIMP2-DX2 protein is stabilized by its direct binding with the HSP70 protein, the AIMP2-DX2 protein becomes unstable and degrades and its level decreases whereas the AIMP2-DX2 protein is dissociated from the HSP70 protein. As a result, the proliferation and differentiation of cells by the AIMP2-DX2 are inhibited. This effect could be confirmed by using siRNA or HSP70 inhibitor which inhibits the expression of HSP70. It is found that the inhibition of the binding between AIMP2-DX2 and HSP70 can inhibit the development and proliferation of cancer cells that are abnormally dividing.

In another embodiment, it was confirmed that the inhibition of the binding between AIMP2-DX2 and HSP70 inhibited cancer cell proliferation, tumor formation and growth through tumorigenesis-related cell experiments and xenograft animal experiments.

Through the above mentioned findings of the present inventors, those skilled in the art may understand that a substance which inhibits a binding or reduce a binding level between AIMP2-DX2 and HSP70 can inhibit the proliferation and differentiation of cancer cells through unstablizing AIMP2-DX2. The representative substance that reduces the binding level of AIMP2-DX2 and HSP70 may include a substance that inhibits the binding itself of AIMP2-DX2 and HSP70, or a substance that decreases the amount of HSP70 protein capable of binding to AIMP2-DX2. A specific example of the anti-cancer agent selected according to the anti-cancer agent screening method of the present invention is described herein in the description of the pharmaceutical composition for preventing or treating cancer according to the present invention.

Step (e) is a step of verifying the anti-cancer activity of the selected test substance in cells or animals.

Specifically, step (e) is a step of determining whether the test substance selected as one decreasing the binding level of AIMP2-DX2 and HSP70 in step (d) has an anti-cancer activity, which is predicted to occur due to the destabilization of AIMP2-DX2 protein, in a cell or animal of a cancer or tumor model. The anti-cancer activity means to inhibit an increase in abnormal cell division, transformation from normal cells into cancer cells, cell division and proliferation of cancer cells, development and growth of tumors, and the like.

The cells or animals of cancer or tumor model can be appropriately selected from those commonly used in the art, and the anti-cancer activity of the substance selected in step (d) can be confirmed. In a specific embodiment of the present invention, xenograft injecting a human cancer cell line into a mouse was used to observe the development and formation process of an in vivo tumor.

The method for screening an anti-cancer agent according to the present invention may further comprise following steps between the steps (d) and (e);

(1) contacting the test substance with a cell expressing AIMP2-DX2;

(2) measuring a protein level of AIMP2-DX2 in the cell and a control cell with which the test substance is not contacted, respectively; and (3) selecting the test substance which reduces the protein level of AIMP2-DX2 in comparison with the control cell.

According to the present invention, it is understood that the protein level of AIMP2-DX2 is decreased when the binding level of AIMP2-DX2 and HSP70 is decreased, because the direct binding of AIMP2-DX2 with HSP70 is required to stabilize AIMP2-DX2 from degradation. The steps (1) to (3) further confirm whether the test substance selected as one decreasing the binding level of AIMP2-DX2 and HSP70 in step (d) decreases the AIMP2-DX2 protein level. The additional steps may be conducted to eliminate a false-positive case even if the test substance was selected as an agent to reduce the binding level of AIMP2-DX2 and HSP70 in step (d), or a case where the level of inhibiting the binding of AIMP2-DX2 to HSP70 is insufficient to cause the destabilization of AIMP2-DX2

Step (1) is a step of contacting the test substance, selected in step (d), with a cell expressing AIMP2-DX2.

The cell expressing AIMP2-DX2 may be a cell expressing AIMP2-DX2 intrinsically, or a cell transformed with a recombinant expression vector comprising a polynucleotide encoding AIMP2-DX2 to overexpress AIMP2-DX2. For example, AIMP2-DX2 destabilizing effect of a test substance can be verified by appropriately selecting among various cancer cell lines expressing AIMP2-DX2. The term 'contacting' means as described above Step (2) is a step of measuring a protein level of AIMP2-DX2 in the cell contacted with the test substance in step (1) and a control cell with which the test substance is not contacted, respectively.

In order to measure the AIMP2-DX2 protein level, a protein detection method commonly used in the art may be selected without limitation. For example, Western blotting, dot blotting, enzyme-linked immunosorbent assay (ELISA), radioimmunoassay (RIA), radial immunodiffusion, Ouchterlony immunodiffusion, rocket immunoelectrophoresis, immunohistochemistry, immunoprecipitation, complement fixation test, flow cytometry (FACS), or protein chip methods may be used.

Step (3) is a step of selecting the test substance which reduces the protein level of AIMP2-DX2 in comparison with the control cell.

The step (3) the AIMP2-DX2 protein level in the cell in contact with the test substance as measured in step (2) is compared with the AIMP2-DX2 protein level in the control cell, and the test substance that is shown to actually reduce AIMP2-DX2 protein level is then screened.

As used herein, the cancer is selected from the group consisting of breast cancer, lung cancer, colon cancer, anal cancer, astrocytoma, leukemia, lymphoma, head and neck cancer, liver cancer, testicular cancer, cervical cancer, sarcoma, hemangioma, esophageal cancer, eye cancer, larynx cancer, oral cancer, mesothelioma, myeloma, oral cavity cancer, rectal cancer, laryngopharyngeal cancer, bladder cancer, uterine cancer, ovarian cancer, prostate cancer, cancer of the large intestine, pancreatic cancer, kidney cancer, stomach cancer, skin cancer, basal cell carcinoma, melanoma, squamous cell carcinoma, oral squamous cell carcinoma, colorectal cancer, glioblastoma, endometrial cancer and malignant glioma, but is not limited thereto.

An embodiment of the present invention also provides a composition for preventing or treating cancer comprising an anti-cancer agent selected by the screening method of the present invention, as an active ingredient.

The present invention also provides a composition for preventing or treating cancer consisting of an anti-cancer agent selected by the screening method of the present invention, as an active ingredient.

The present invention also provides a composition for preventing or treating cancer consisting essentially of an anti-cancer agent selected by the screening method of the present invention, as an active ingredient.

The anti-cancer agent selected according to the method of the present invention includes any substance as long as it is capable of reducing the binding level of AIMP2-DX2 and HSP70 and destabilizing AIMP2-DX2 protein to inhibit the proliferation and differentiation of cancer cells, while there is no particular limitation on the properties of the substance, however, a substance may be considered which inhibits the binding itself of two proteins, AIMP2-DX2 and HSP70, or which inhibits the expression of HSP70 and lowers the level of AIMP2-DX2 protein capable of binding to HSP70.

The anti-cancer agent selected by the method of the present invention may, be selected from the group consisting of siRNA, shRNA, miRNA, ribozyme, DNAzyme, peptide nucleic add (PNA), antisense oligonucleotide, antibody, aptamer, peptide, natural extracts and chemical substance.

The present inventors have found that the inhibition of HSP70 expression in cancer cells by using siRNA (si-HSP70) or HSP70 inhibitor specific to HSP70 reduces the level of AIMP2-DX2 bound to HSP70, while the AIMP2-DX2 protein is degraded and decreased in its level confirming that the proliferation and differentiation of cancer cells by AIMP2-DX2 are inhibited.

This results shows that an agent capable of inhibiting the expression of HSP70, such as siRNA or HSP70 inhibitor, can be effectively used for the prevention and treatment of cancer diseases.

Therefore, the anti-cancer agent selected by the screening method according to the present invention may include siRNA, shRNA or HSP70 inhibitor specific to HSP70. The siRNA or shRNA is composed of 10 to 30 nucleotide sequences which is capable of specifically binding to and inducing degradation of HSP70 mRNA. The siRNA or shRNA can be easily prepared by a person skilled in the art according to a method known in the art.

In a specific embodiment of the present invention, it was confirmed that a compound of the following Formula 1 inhibits the binding of AIMP2-DX2 and HSP70 in a concentration-dependent manner, resulting in the destabilization of AIMP2-DX2 and the inhibition of its expression, thereby inhibiting the proliferation and differentiation of cancer cells:

[Formula 1]

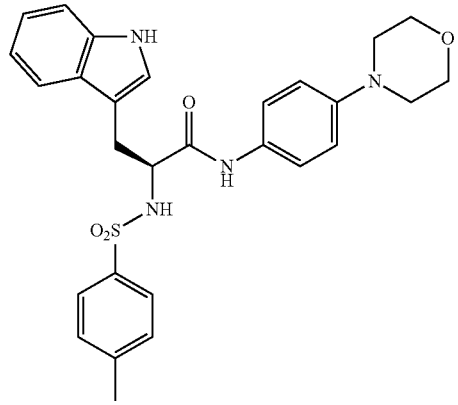

BC-DXI-495

The pharmaceutical composition for preventing or treating cancer according to the present invention may be administered orally or parenterally. The parental administration may be, but is not limited to, intravenous, intramuscular, intra-arterial, intramedullary, intradural, intracardiac, transdermal, subcutaneous, intraperitoneal, intranasal, intestinal, topical, sublingual, or rectal administration while being preferably intravascular administration.

In addition, the pharmaceutical composition for preventing or treating cancer according to the present invention may be variously formulated, together with a pharmaceutically acceptable carrier, depending on the route of administration, by a method known in the art. The term "pharmaceutically acceptable" refers to a non-toxic one that is physiologically acceptable, does not inhibit the effect of an active ingredient when administered to humans, and does not usually induce an allergic reaction or similar reactions, such as gastroenteric troubles and dizziness. The carrier includes all kinds of solvents, dispersion media, oil-in-water or water-in-oil emulsions, aqueous compositions, liposomes, microbeads, and microsomes.

When parenteral administered, the pharmaceutical composition of the present invention may be formulated, together with a suitable parenteral carrier, in a dosage form of an injection, a transdermal agent or preparation, and a nasal inhalant, by a method known in the art. The injection needs to be essentially sterilized, and needs to be protected from the contamination of microorganisms, such as bacteria and fungus. Examples of the suitable carrier for the injection may include, but are not limited to, solvents or dispersion media, including water, ethanol, polyols (e. g., glycerol, propylene glycol, liquid polyethylene glycol, etc.), mixtures thereof, and/or vegetable oils. More preferably, Hanks' solution, Ringer's solution, phosphate buffered saline (PBS) or sterile water for injection containing triethanolamine, or an isotonic solution (such as 10% ethanol, 40% propylene glycol, or 5% dextrose) may be used as a suitable carrier. In order to protect the injection from microbial contamination, the injection may further contain various antibiotic and antifungal agents, such as paraben, chlorobutanol, phenol, sorbic acid, and thimerosal. In most cases, the injection may further contain an isotonic agent, such as sugar or sodium chloride.

The form of the transdermal agent or preparation includes ointment, cream, lotion, gel, solution for external application, paste, liniment, and aerosol. The term "transdermal administration" means the delivery of an effective amount of an active ingredient, contained in the pharmaceutical composition, into the skin through its topical administration to the skin. For example, the pharmaceutical composition of the present invention is prepared in a dosage form of an injection, which may be then administered by slightly pricking the skin with a 30-gauge needle or being directly applied to the skin. These dosage forms are described in the literature, which is a formulary generally known in pharmaceutical chemistry (Remington's Pharmaceutical Science, 15th Edition, 1975, Mack Publishing Company, Easton, Pa.).

In the case of an inhalation agent or preparation, the composition according to the present invention may be conveniently delivered in the form of an aerosol spray from a pressurized pack or a sprayer, using a suitable propellant, for example, dichlorofluoromethane, trichlorofluoromethane, dichlorotetrafluoroethane, carbon dioxide, or other suitable gas. In the case of a pressurized aerosol, a dosage unit may be determined by providing a valve that delivers a measured quantity. For example, a gelatin capsule and a cartridge used in an inhaler or an insufflator may be formulated to contain a compound, and a powder mixture of proper powder materials, such as lactose or starch.

Other pharmaceutically acceptable carriers may be referenced in the following literature (Remington's Pharmaceutical Sciences, 19th ed., Mack Publishing Company, Easton, Pa., 1995).

In addition, the pharmaceutical composition according to the present invention may further contain one or more buffers (for example, saline solution or PBS), carbohydrates (for example, glucose, mannose, sucrose, or dextran), antioxidants, bacteriostatic agents, chelating agents (for example, EDTA or glutathione), adjuvants (for example, aluminum hydroxide), suspension agents, thickeners, and/or preservatives.

In addition, the pharmaceutical composition of the present invention may be formulated by a method known in the art such that the pharmaceutical composition can provide rapid, sustained, or delayed release of active ingredients after its administration into mammals. In addition, the pharmaceutical composition of the present invention may be administered in combination with a known compound having an effect of preventing or treating cancer.

The present invention provides use of an anti-cancer agent selected by the screening method for the preparation of an agent for preventing or treating a cancer.

The present invention provides a method for treating a cancer in a subject, the method comprising administering an effective amount of an anti-cancer agent selected by the screening method to a subject in need thereof.

As used herein, the term "effective amount" refers to an amount exhibiting an effect of alleviating, treating, preventing, detecting, or diagnosing cancer or an effect of inhibiting or reducing the metastasis of cancer, while the term "subject" refers to an animal, preferably, a mammal, and especially, an animal including a human being, and may be a cell, tissue, and organ, or the like originating from an animal. The subject may be a patient in need of such an effect.

As used herein, the term "treatment" broadly refers to alleviating cancers, a cancer-related diseases, or a symptom of the cancer-related diseases, and may include healing, substantially preventing, or alleviating the condition of these diseases, and may include alleviating, curing, or preventing one or most of the symptoms resulting from cancer or cancer-related diseases, while not being limited thereto.

The term "comprising" is used synonymously with "containing" or "being characterized", and does not exclude additional ingredients or steps that are not mentioned in the compositions and the methods. The term "consisting of" excludes additional elements, steps, or ingredients that are not separately described. The term "consisting essentially of" means that in the scope of the compositions or methods, the term includes any material or step that does not substantially affect basic characteristics of the compositions or methods, as well as described materials or steps.

Advantageous Effect

Accordingly, based on the discovery that HSP70 binds directly with and stabilizes AIMP2-DX2, one of the major causative proteins of cancer the present invention provides, an anti-cancer agent screening method that selects a substance that reduces the binding level of AIMP2-DX2 and HSP70 as an anti-cancer agent using an AIMP2-DX2 or a fragment thereof and HSP70 or a fragment thereof, and a composition for preventing or treating cancer comprising an anti-cancer agent selected by the screening method as an active ingredient. In accordance with the present invention, an agent for inhibiting the expression of HSP70 such as siRNA, and shRNA, and a compound that inhibits the binding of HSP70 to AIMP2-DX2 are excellent in lowering the level of AIMP2-DX2 protein in cancer and inhibiting the development and progression of cancer.

BRIEF DESCRIPTION OF DRAWINGS/FIGURES

The patent or application file contains at least one drawing executed in color. Copies of this patent or patent application publication with color drawing(s) will be provided by the Office upon request and payment of the necessary fee.

DX2 shown in each drawing is an abbreviation of AIMP2-DX2.

FIG. 2B shows the results of immuno-precipitation (IP) and Western blotting confirming an increase in the binding of endogenous AIMP2-DX2 to HSP70 protein by treatment with EGF (WCL: whole cell lysate).

Figure 9A:
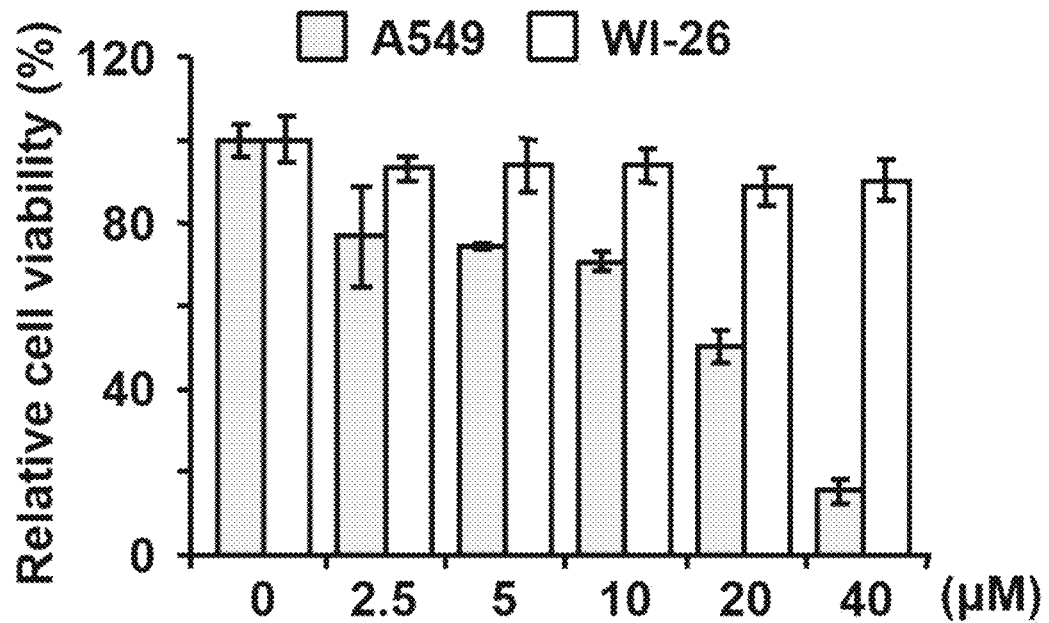
FIG. 9A shows the results of evaluating cell survival rate, after the treatment of BC-DXI-495 compound in a concentration-dependent manner on A549 cell line, lung cancer cell line and WI-26 cell line, normal lung cell line, respectively.
Figure 9B:
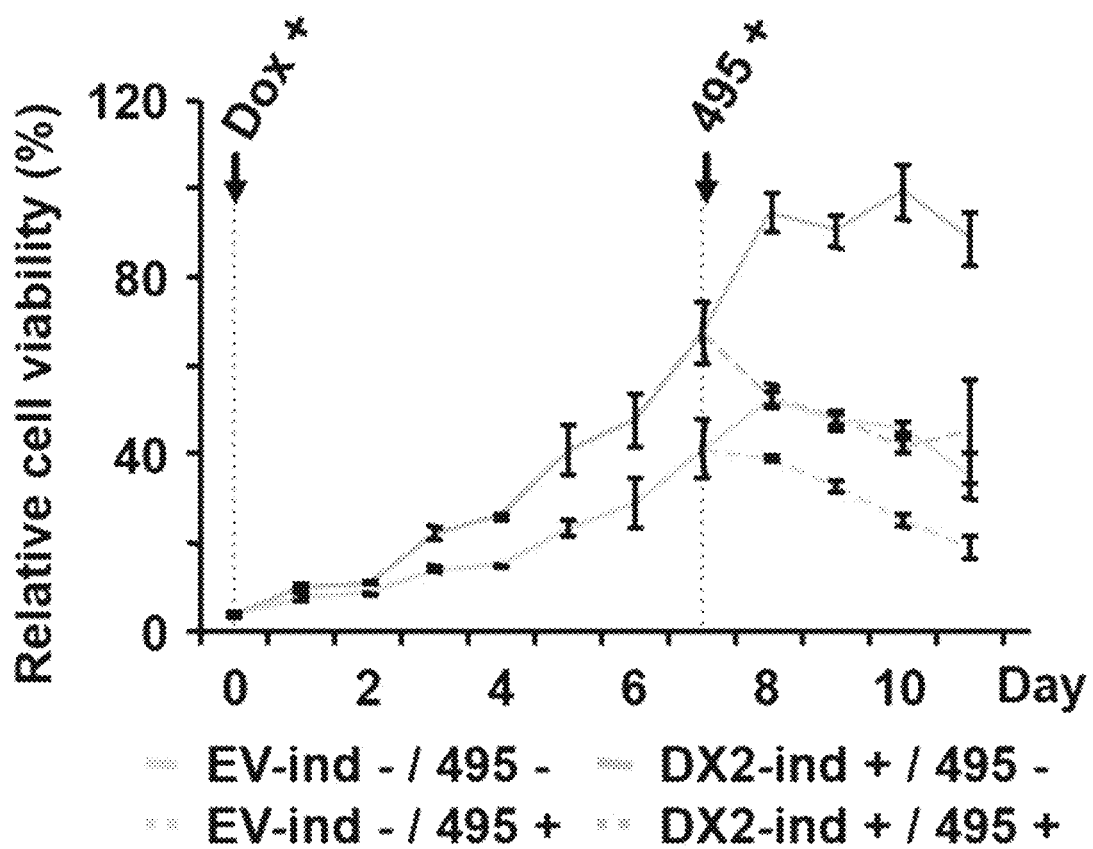
FIG. 9B shows the results of inducing a cell growth by AIMP2-DX2 by treating doxycycline (0.5 mg/ml) on A549, a lung cancer cell capable of inducing AIMP2-DX2 expression by doxycycline (Sigma), followed by the treatment of BC-DXI-495 (40 uM) on day 7, to verify the inhibition of cell growth and death for 96 hours.
Figures 9C, 10A:
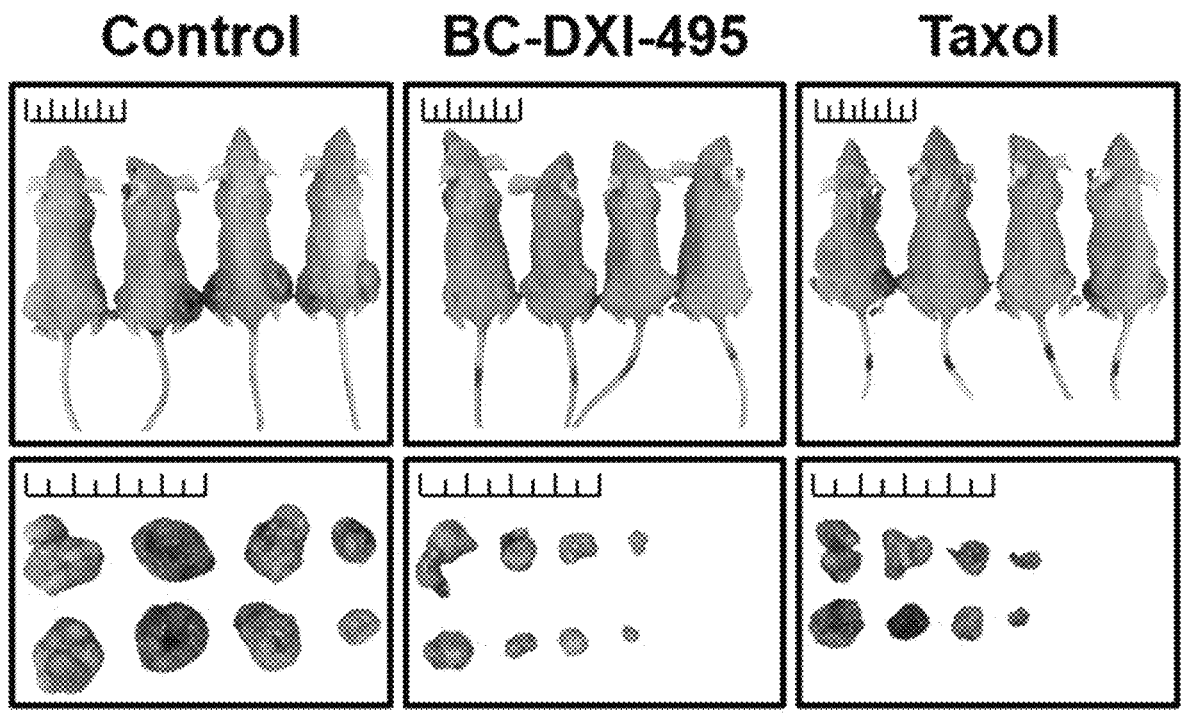
FIG. 9C shows the result of calculating the GI50 by MTT assay, after treatment of BC-DXI-495 compound on two lung normal cells (WI-26, WI-38) and seven lung cancer cells (NCI-H2087, HCC-1359, HCC-95, HCC-366, HCC-1438, HCC-1588, NCI-H460) with different AIMP2-DX2 expression levels, respectively.
Figure 10B:
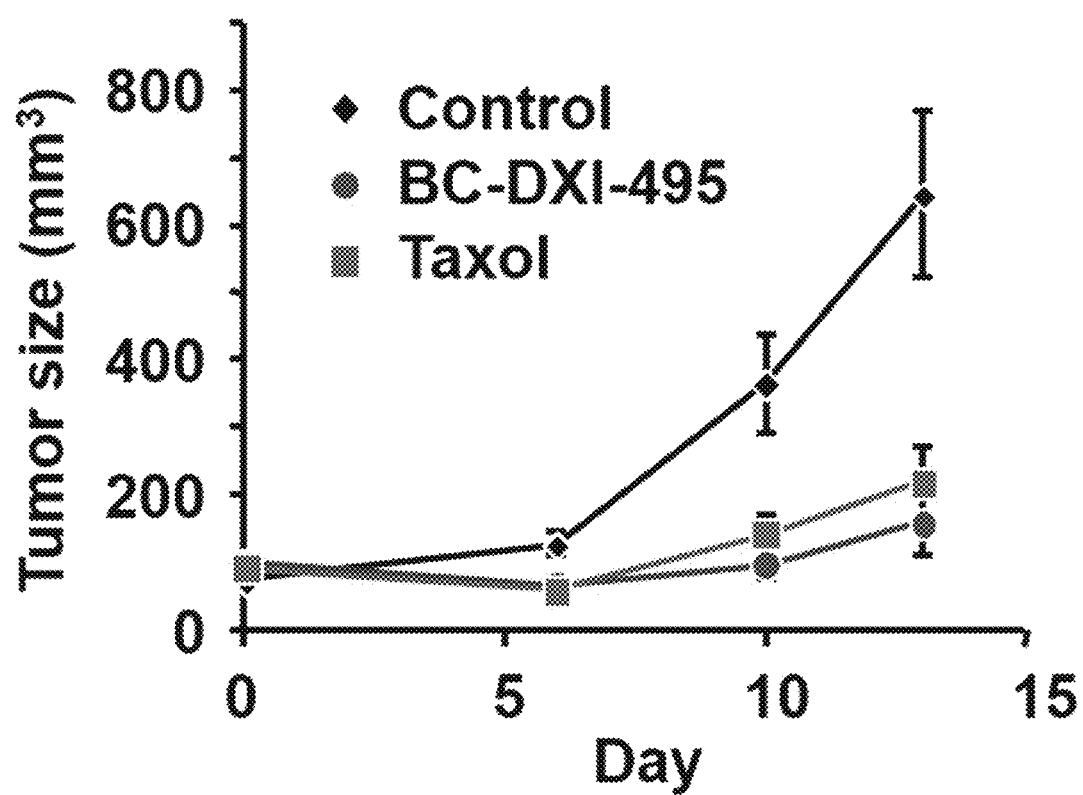
Figure 10C:
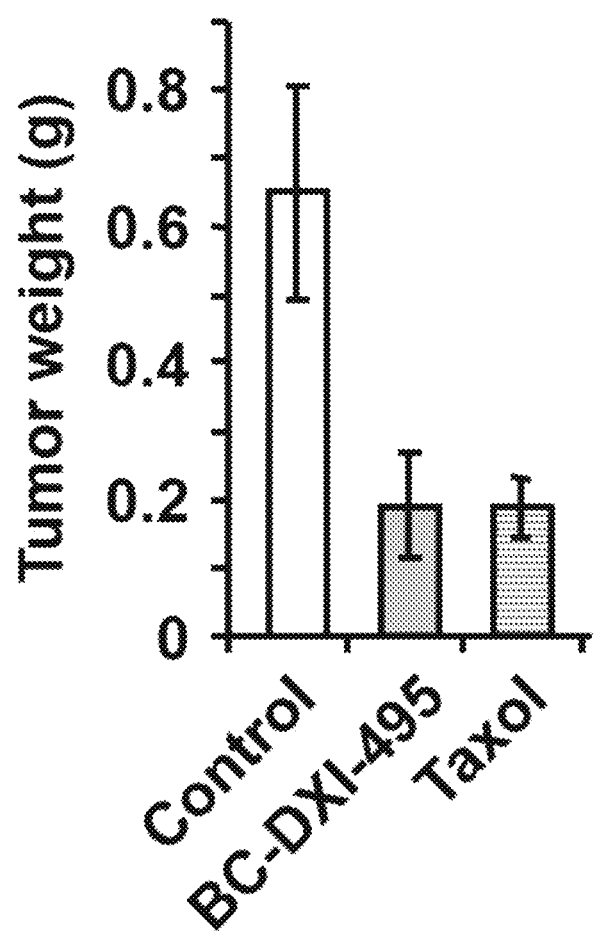
Figure 10D:
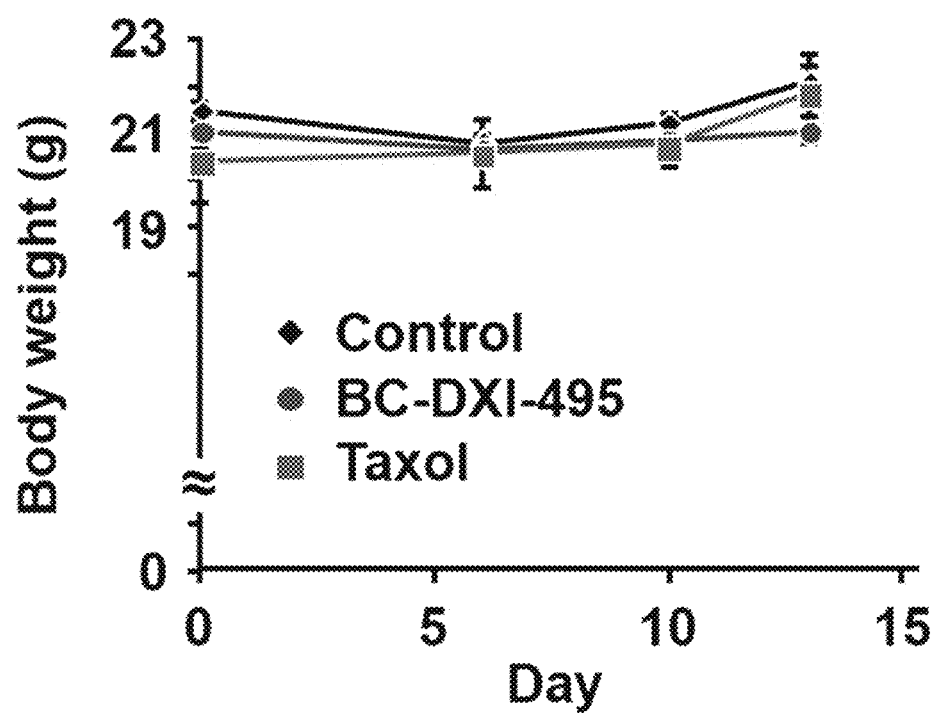

FIGS. 10A, 10B, 10C, and 10D show the results of observation of changes in tumor size after H460 cells with high expressing AIMP2-DX2 were xenografted in a mouse, followed by administering BC-DXI-495 compound or Taxol (FIG. 10A: visual observation of tumor, FIG. 10B: volume change of tumor, FIG. 10C: weight change of tumor, FIG. 10D: body weight change of animal).

MODE FOR CARRYING OUT INVENTION

Hereinafter, the present invention will be described in detail.

However, the following examples are only illustrative of the present invention, and the present invention is not limited to the following examples.

Example 1: Analysis of Association Between AIMP2-DX2 and HSP70

The lysates of 293T cells expressing strep-AIMP2-DX2 and strep-AIMP2 were immunoprecipitated (IP) using a strep-tag column (GE Healthcare), and then proteins precipitated by the column were separated by SDS-PAGE. Separated proteins were degraded to their peptide levels by in-gel digestion using trypsin (Hyclone), and these peptides were analyzed by LC-mass spectrometry (Thermo) (FIG. 1A).

293T cells were supplied from ATCC. Strep-AIMP2-DX2 and strep-AIMP2 were cloned by DX2 and AIMP2 into pEXPR-IBA5 vector, respectively and DX2 and AIMP2 were overexpressed in 293T cells using a transfection reagent sold under the tradename TURBOFECT™ (Thermo).

Cell lysis was performed by incubating at 4° C. for 30 min with an appropriate amount of lysis buffer (50 mM Tris (pH7.4), 100 mM NaCl, 10% Glycerol, 1 mM EDTA, 0.5% of a reagent sold under the tradename TRITON™ X-100, PBS). And, lysed cell lysate was centrifuged at 13,200 rpm for 15 minutes. After removing the supernatant from the cell lysate, the supernatant was passed through a strep-tag column (thermo). After passing the supernatant, the proteins bound to the column were eluted by using elution buffer, and then the collected proteins were separated by SDS-PAGE.

Figure 1A:
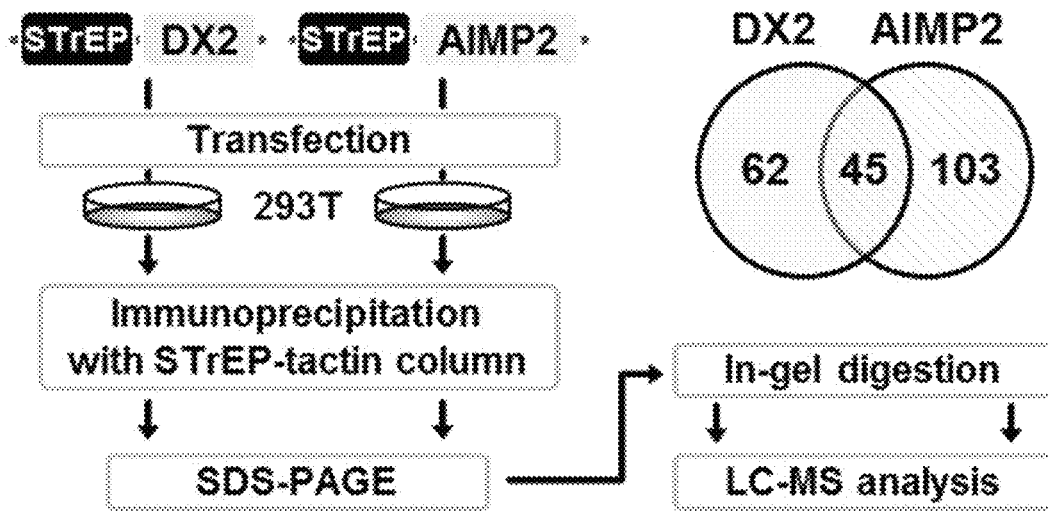
FIG. 1A is a schematic diagram showing a result of mass spectrometry analysis of the correlation between AIMP2-DX2 and AIMP2.

As shown in FIG. 1A, the interaction between AIMP2-DX2 and AIMP2 was analyzed by mass spectrometry. As a result, 107 proteins binding to AIMP2-DX2 and 148 proteins to AIMP2 were identified, respectively, while confirming that 45 binding proteins among them overlap.

Figure 1B:
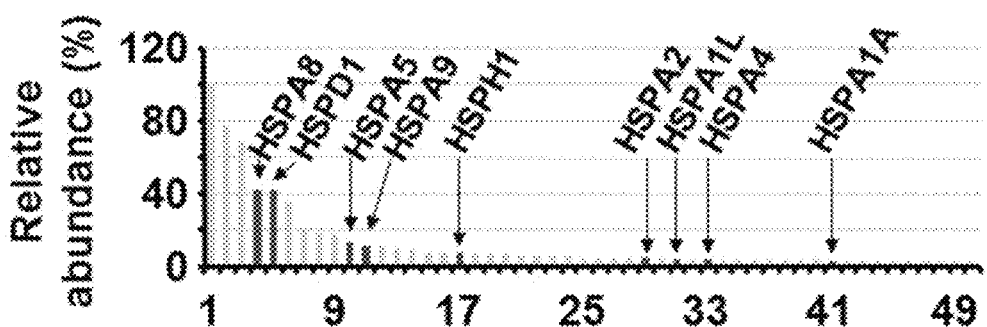
FIG. 1B shows the results of mass analysis of the binding of HSP70 isoforms to AIMP2-DX2 or AIMP2 (red bars: AIMP2-DX2, blue bars: AIMP2).
Figure 1B:
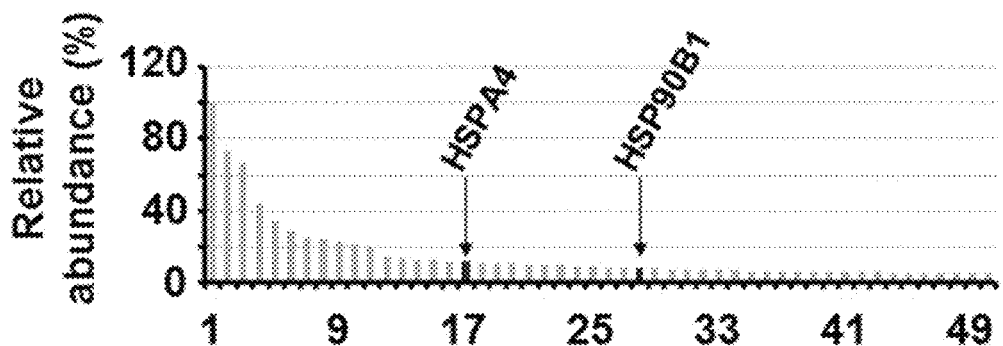

Meanwhile, as shown in FIG. 1B, it was confirmed that HSP70 protein binds predominantly to AIMP2-DX2 as compared to AIMP2.

More specifically, the red graph in FIG. 1B is a growth showing proteins binding to AIMP2-DX2, while the blue graph is a graph showing proteins binding to AIMP2. In the mass analysis, the more detection, the more left marked on the horizontal axis of the graph, and the higher frequency displayed on the vertical axis. In the red graph of FIG. 1B, HSPA8, HSPD1, HSPA5, HSPA9, HSPH1, HSPA2, HSPA1L, HSPA4 and HSPA1A, all of which are designated as AIMP2-DX2 binding proteins, are isoforms of HSP70. On the other hand, in the blue graph AIMP2, only one isoform (HSPA4) of HSP70 was detected. In addition, in the case of AIMP2, HSP90B1, an isoform of HSP90 that was not observed in DX2, was detected. As a result, it was concluded that HSP70 binds predominantly to AIMP2-DX2.

Example 2: Confirmation of the Binding Relationship Between AIMP2-DX2 and HSP70

H460 cells were treated with endothelial growth factor (EGF (Peprotech)) for 30 minutes, and then lysed with IP buffer (50 mM Tris (pH7.4), 100 mM NaCl, 10% Glycerol, 1 mM EDTA, 0.5% of a reagent sold under the tradename TRITON™ X-100, PBS) at 4° C. for 30 minutes. IP was conducted on cell lysate using Hsp70 antibody (Abcam). After IP, DX2, AIMP2 and HSP70 proteins were identified by SDS-PAGE and western blotting. Actin (Sigma) means loading control, and WCL means whole cell lysate.

Figure 2A:
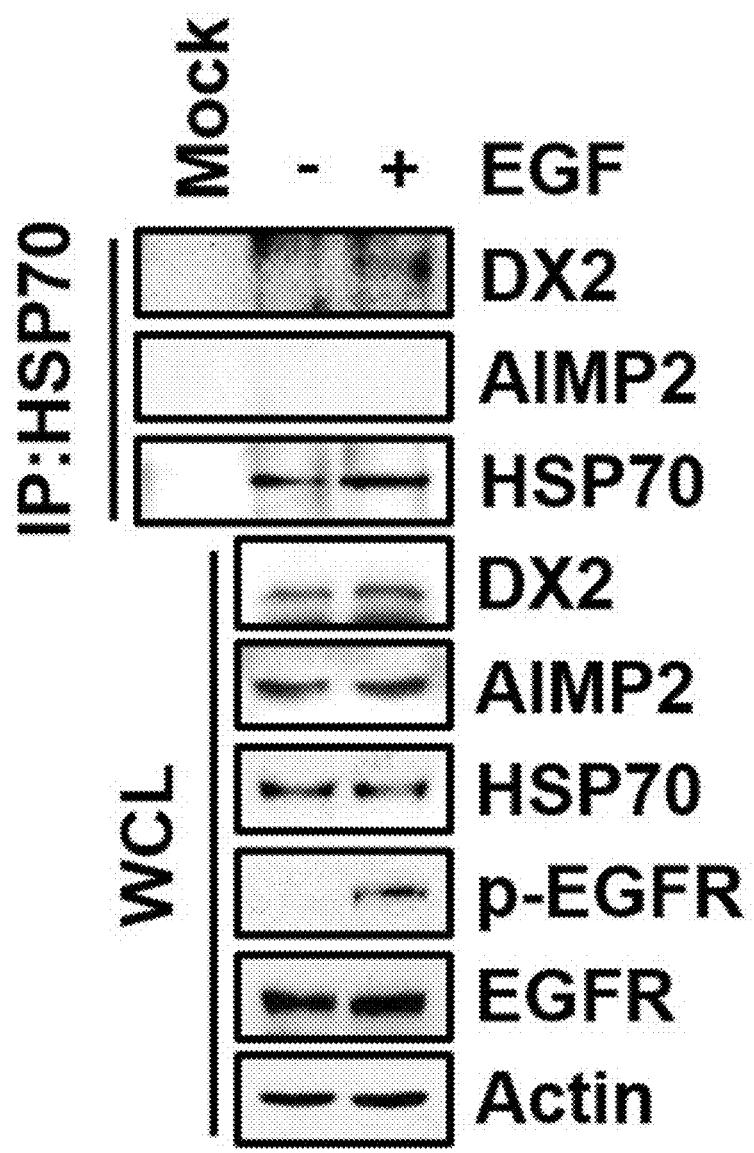
FIG. 2A shows the results of immuno-precipitation (IP) and Western blotting confirming an increase in the binding of endogenous HSP70 to AIMP2-DX2 protein by the treatment of EGF (WCL: whole cell lysate).

As shown in FIG. 2A, it was confirmed that the binding of endogenous HSP70 to AIMP2-DX2 protein increases by EGF treatment, while it was found that AIMP2 does not bind to HSP70.

293T cells overexpressing Strep-AIMP2-DX2 were treated with EGF for 30 minutes. After the cells were lysed in the same manner as described above, IP was performed using a Strep-tag column (GE Helathcare). After IR the amount of Strep-AIMP2-DX2, HSP70 and HSP90 were confirmed by SDS-PAGE and western blotting. These proteins were identified using StrepMAB-Classic-HRP (IBA), HSP70 specific antibody (Santa Cruz), and HSP90 specific antibody (Santa Cruz).

As shown in FIG. 2B, it was confirmed that the binding of exogenous AIMP2-DX2 to HSP70 protein increases by EGF treatment, while the binding of HSP90 to AIMP2-DX2 is very weak and is not increased by EGF.

293T cells overexpressing both RFP-AIMP2-DX2 and GFP-HSP70 were treated with EGF for 30 minutes. After EGF treatment, the cells were washed 3 times with cold PBS, and were fixed with cold methanol for 10 minutes. After fixation, the cells were washed 3 times with cold PBS, and nuclei were stained with DAPI (Invitrogen) solution. After staining, each fluorescence was observed using confocal microscopy.

Figure 2C:
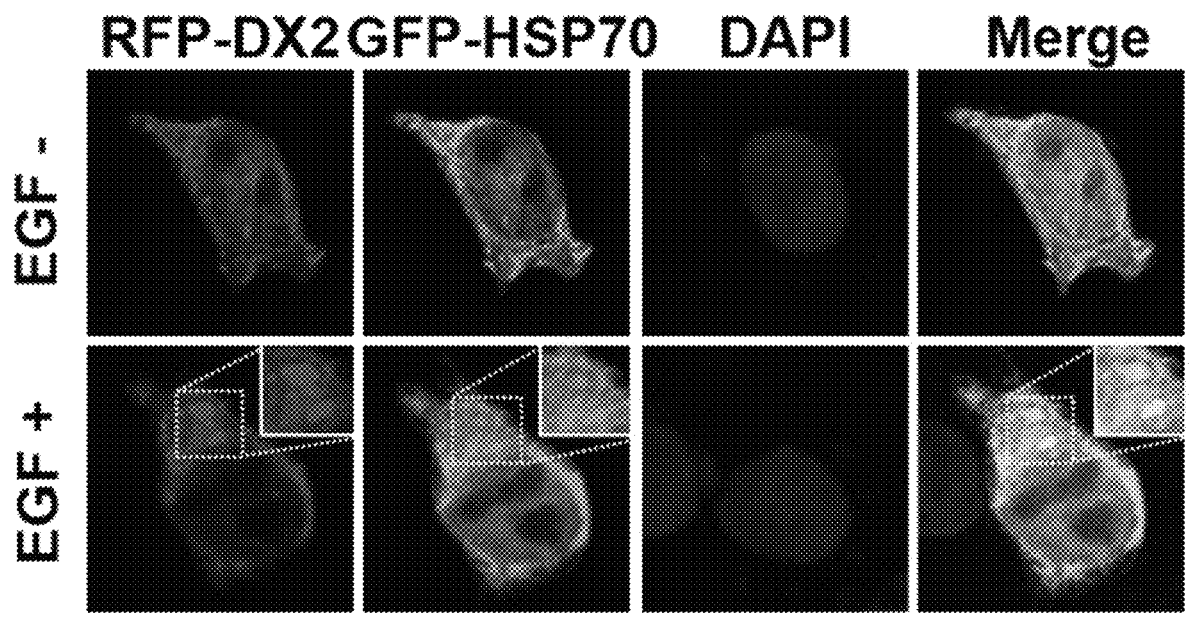
FIG. 2C shows the result of confocal microscopy confirming an increase in binding of RFP-AIMP2-DX2 and GFP-HSP70, after the treatment of 293T cells overexpressing RFP-AIMP2-DX2 and GFP-HSP70 with EGF for 30 minutes.

As shown in FIG. 2C, it was confirmed by confocal microscopy that the binding of RFP-AIMP2-DX2 and GFP-HSP70 increases by EGF treatment.

Binding between HSP70 protein and AIMP2-DX2 protein was analyzed by surface plasmon resonance (SPR, GE) equipment. After the HSP70 protein was fixed, the AIMP2-DX2 protein was flowed by concentration. The binding and separation values of the respective proteins were obtained, and the KD value was calculated.

Figure 2D:
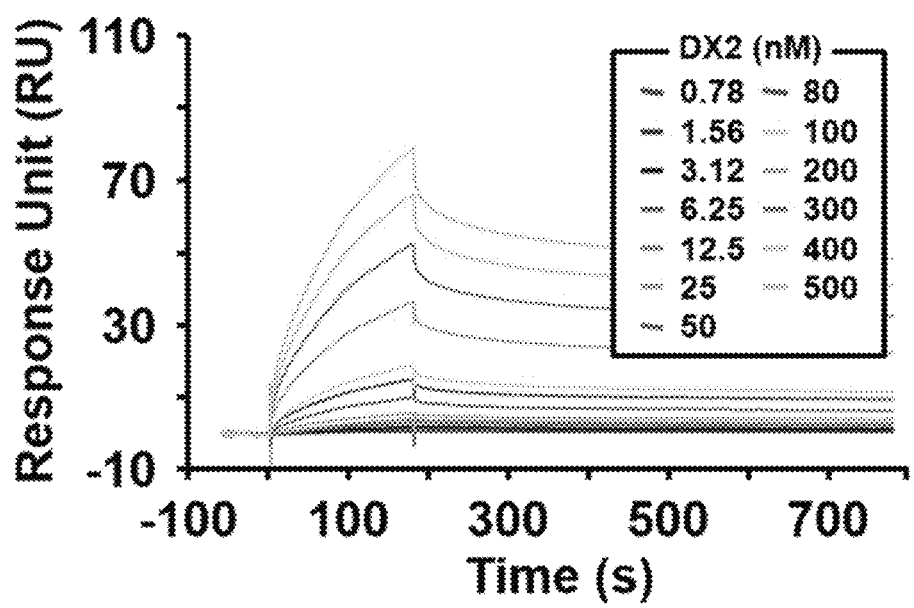
FIG. 2D shows the result of evaluating the binding KD value of AIMP2-DX2 and HSP70 using surface plasmon resonance (SPR) device.

As shown in FIG. 2D, the direct binding of the purified AIMP2-DX2 and HSP70 proteins was observed at a KD value of $4.79 \times 10^{-1 \circ}$, through SPR assay.

Example 3: Analysis of Combination Structure of AIMP2-DX2 and HSP70

AIMP2-DX2 protein fragments (DM1 to DM5) fused with GST-tag and 293T cell lysate were mixed. After mixing, each AIMP2-DX2 protein was pulled down using a reagent sold under the tradename glutathione-SEPHAROSE™ (GE Healthcare). The amount of HSP70 proteins pulled down with AIMP2-DX2 protein was confirmed by mass spectrometry. The amino acid positions of the AIMP2-DX2 protein fragments used in the experiment are shown in FIG. 3A.

Figures 3A, 3B:
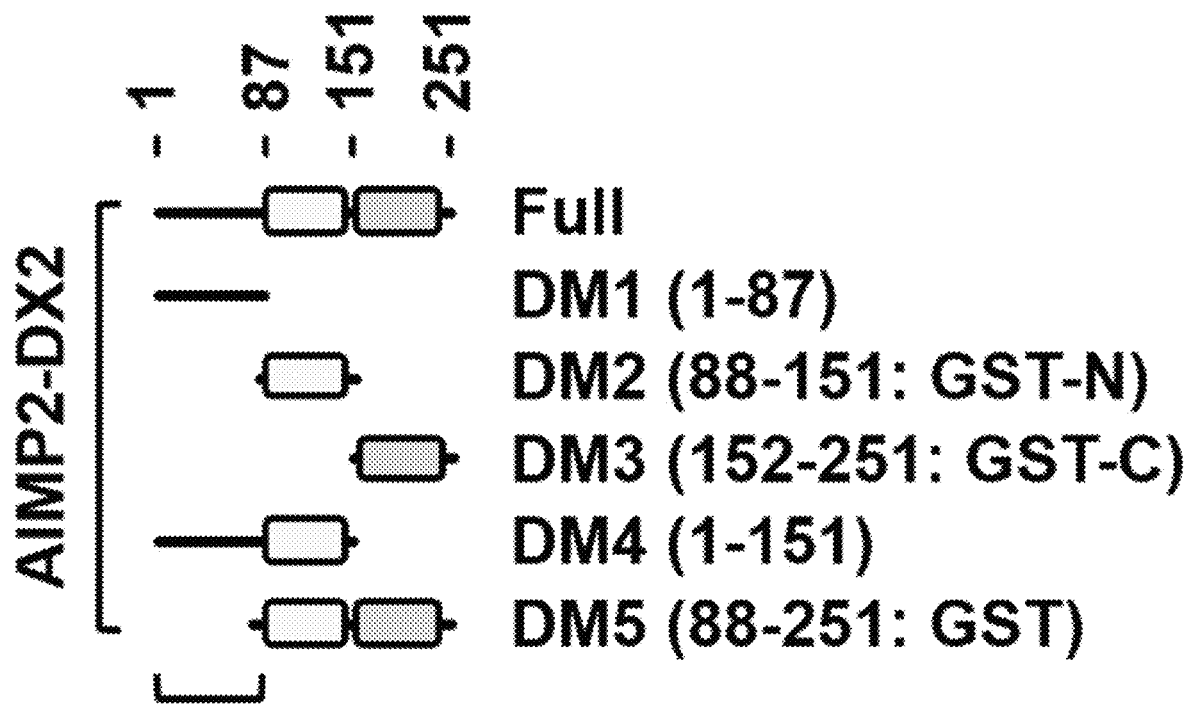
FIG. 3A is a schematic diagram showing fragments of the AIMP2-DX2 protein and their abbreviations.
FIG. 3B shows the results of measuring the binding degree of HSP70 isoforms (HSPA1A, HSPA4, HSPA5, HSPA8, HSPA9, HSPD1) to each fragment of AIMP2-DX2, respectively.

As shown in FIG. 3B, among the AIMP2-DX2 protein fragments, the predominant binding of HSP70 families to DM1 (a fragment corresponding to 1-87 amino acid residues of the amino acid sequence of SEQ ID NO: 1) having the amino acid sequence of SEQ ID NO: 2 was confirmed by mass spectrometry.

Next, an experiment was performed to specifically confirm the binding structure between AIMP2-DX2 and HSP70.

GST-EV, GST-AIMP2-DX2 full and GST-AIMP2-DX2 fragments (DM1~DM5) were mixed with 293T cell lysate overexpressing GFP-HSP70. After mixing, the GST protein was pulled down using a reagent sold under the tradename glutathione-SEPHAROSE™, and proteins pulled down were analyzed by SDS-PAGE and western blot. GFP protein was identified using GFP-specific antibodies, while GST protein was identified by coomassie staining.

Figure 3C:
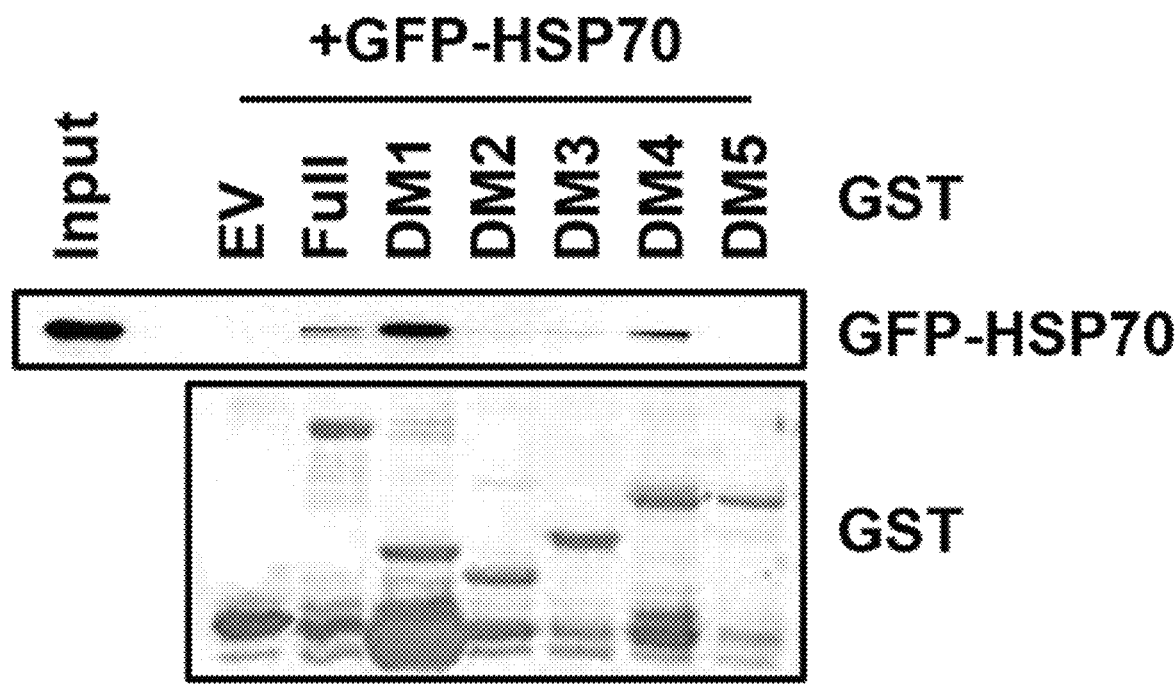
FIG. 3C shows the results of western blot analysis on the binding degree of each fragment of AIMP2-DX2 binds to HSP70, respectively.
Figure 3D:
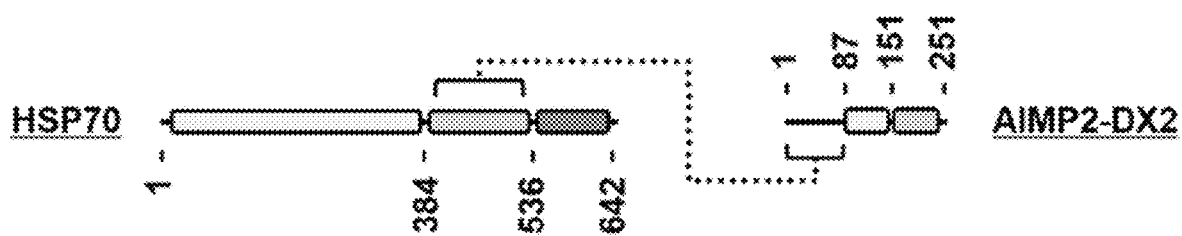
FIG. 3D is a schematic diagram showing binding positions of AIMP2-DX2 and HSP70 in each protein, respectively.

As shown in FIGS. 3C and 3D, it was found that the DM1 fragment, which has the amino acid sequence of SEQ ID NO: 2 comprising 1-87 amino acids of the AIMP2-DX2 protein, binds to HSP70.

Meanwhile, an experiment was performed to confirm a portion of HSP70 protein which binds to AIMP2-DX2.

Figure 3E:
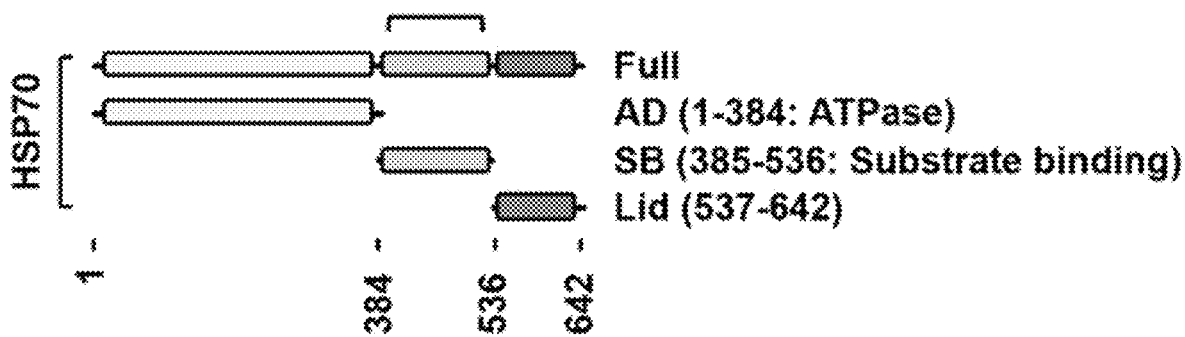
FIG. 3E is a schematic diagram showing fragments of the HSP70 protein and their abbreviations.

With Strep-AIMP2-DX2, GFP-HSP70 full and GFP-HSP70 fragments (AD, SB, Lid) were overexpressed in 293T cells. Then, IP was performed on the lysate of 293T cells using a strep-tag column. The IP-performed proteins with Strep-AIMP2-DX2 were separated by SDS-PAGE, and the binding of each GFP protein was confirmed by western blot using GFP-specific antibody. The amino acid positions in the HSP70 protein of the respective fragments (AD, SB, Lid) used in the experiments are shown in FIG. 3E.

Figure 3F:
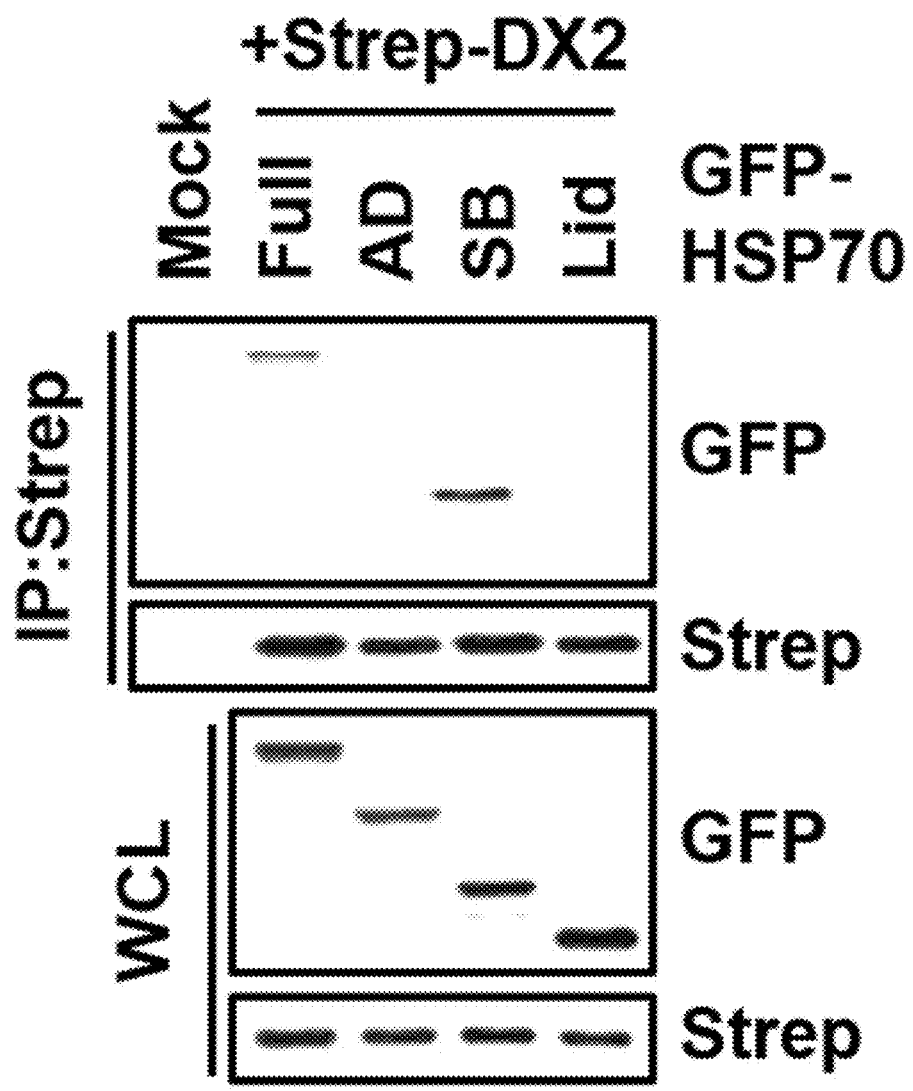
FIG. 3F shows the results of western blot analysis on a fragment binding to AIMP2-DX2 among fragments of HSP70 protein (WCL: whole cell lysate).
Figure 4:
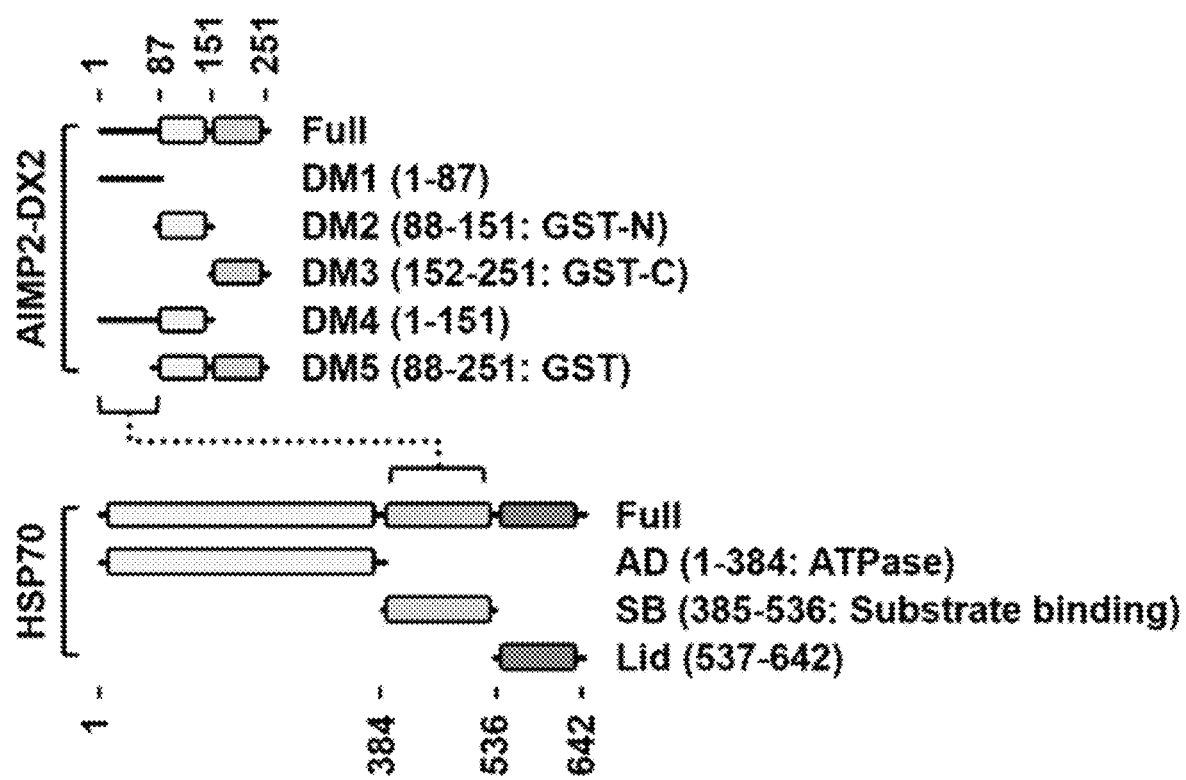
FIG. 4 is a schematic diagram showing a binding position of each protein in a binding relationship between AIMP2-DX2 and HSP70.

As shown in FIG. 3F and FIG. 4, only a fragment comprising the SB (substrate binding domain) portion having the amino acid sequence of SEQ ID NO: 4 among the HSP70 protein fragments was found to bind to AIMP2-DX2.

Example 4: Increased Stabilization of AIMP2-DX2 by HSP70

GFP-EV and GFP-HSP70 were over-expressed by transfection into H460 cells. In addition, HSP70-specific si-RNA (si-HSP70, Santa Cruz) was used to reduce the expression of HSP70, while si-control (Invitrogen) was used as a control. The protein expression level of H460 cells, in which the expression of HSP70 was increased or decreased, was confirmed by Western blotting and the mRNA expression level was confirmed by RT-PCR. The HSP70 specific primer sequence was used as follows: F: GCG TAA TAC GAC TCA CTA TAG GGA GAA TGC CCC CAG CTA CGT GGC CTT C (SEQ NO ID: 5), R: GCG TAA TAC GAC TCA CTA TAG GGA GAT AAA GCT TGG CGT CGC GCA GAG C (SEQ NO ID: 6).

Figure 5A:
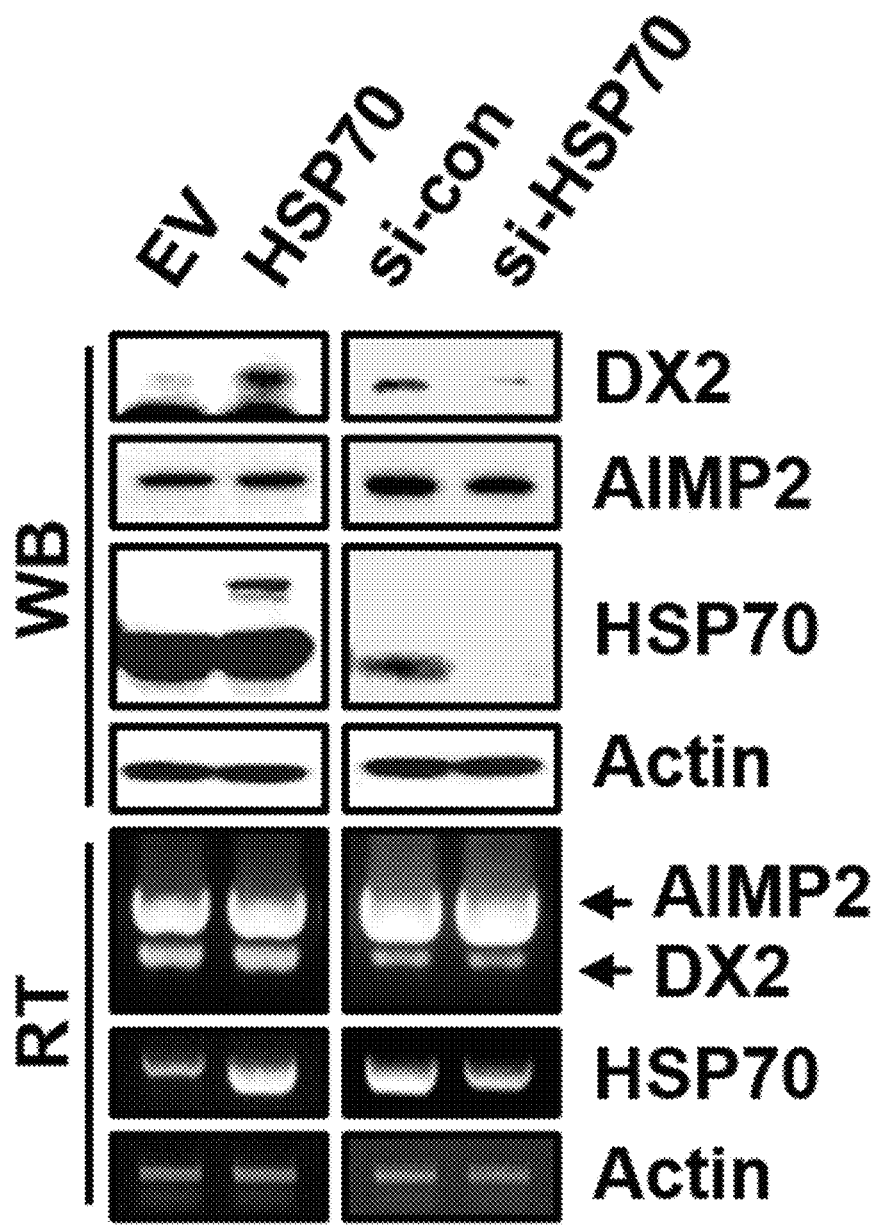
FIG. 5A shows the results of observing changes in expression of AIMP2-DX2 at protein and gene levels, respectively, when HSP70 protein was treated with cells or when si-HSP70 was treated to inhibit HSP70 expression (WB: western blot, RT: RT-PCR).

As shown in FIG. 5A, AIMP2-DX2 protein was increased by overexpression of HSP70, whereas AIMP2-DX2 protein was decreased by reduction of HSP70 through si-RNA technique. At this time, since the transcription of AIMP2-DX2 was not affected, it was found that the regulation of AIMP2-DX2 by HSP70 occurs after transcription, that is, at a protein level.

Meanwhile, H460 cells were treated with the HSP70 inhibitors Pifithrin-u (Tocris) and VER155008 (Sigma), and the HSP90 inhibitors Geldanamycin (Tocris) and PUH71 (Tocris), respectively, and then, western blot and RT-PCR were used to confirm protein and mRNA expression levels. The expression level of AIMP2-DX2 protein was confirmed using AIMP2-DX2 specific antibody (Cell signaling).

Figure 5B:
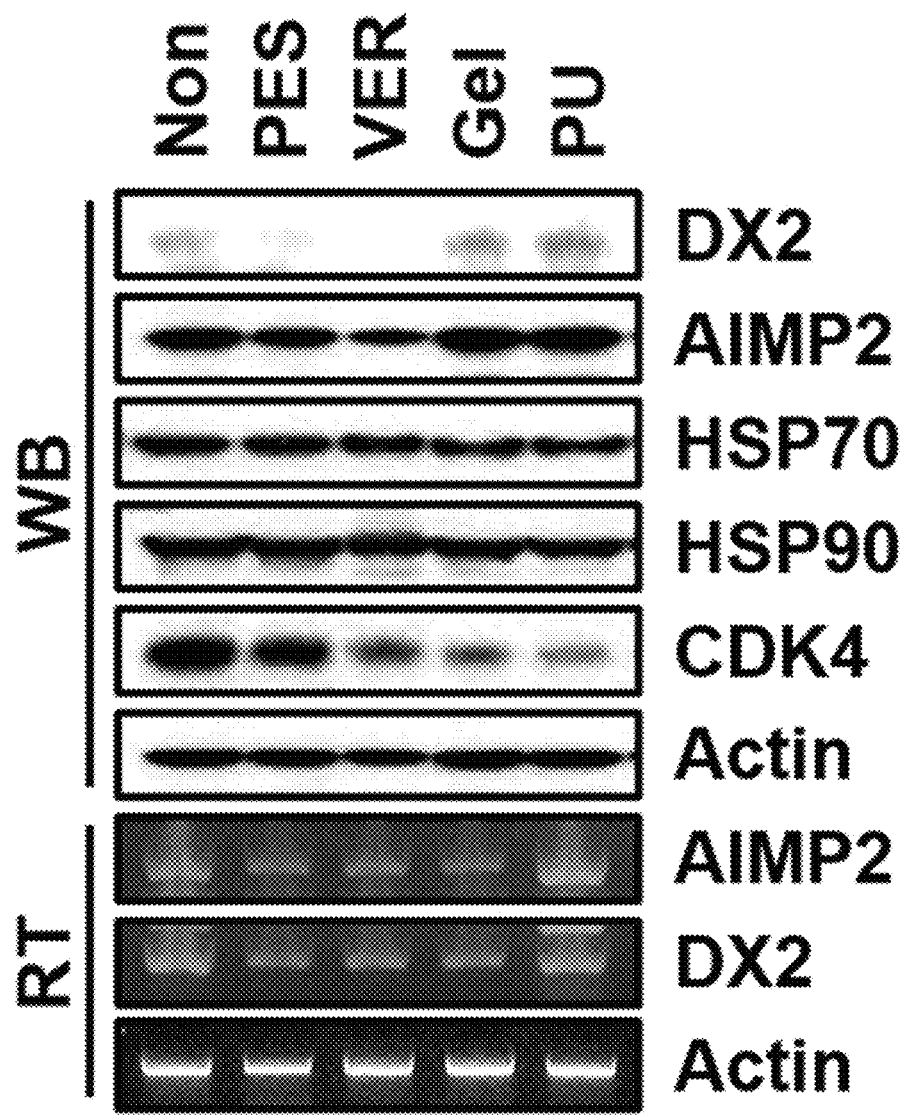
FIG. 5B shows the results of observing changes in the expression of AIMP2-DX2 at protein and gene levels, when H460 cells were treated with HSP70 inhibitors PES (Pifithrin-u), VER (VER155008) or with HSP90 inhibitors Gel (Geldanamycin) and PU (PUH71), respectively (WB: western blot, RT: RT-PCR).

As shown in FIG. 5B, the expression level of AIMP2-DX2 protein was decreased by the treatment with PES (Pifithrin-u) and VER (VER155008), which are HSP70 inhibitors. The expression level of AIMP2-DX2 protein was not affected by HSP90 inhibitor Gel (Geldanamycin) and PU (PUH71) treatment, while the expression level of AIMP2 was not affected by HSP70 and HSP90 inhibitors. Furthermore, since the transcription of AIMP2-DX2 was not affected by each inhibitor treatment, it was found that the regulation of AIMP2-DX2 by HSP70 inhibitor treatment occurs after transcription, that is, at a protein level.

From the above results, it was determined that HSP70 specifically stabilizes AIMP2-DX2 protein.

Example 5: Cell Division Regulation of HSP70 Via DX2

The HSP70 inhibitors Pifithrin-u (PES), and VER155008 (VER) and the HSP90 inhibitors Geldanamycin (Gel) and PUH71(Pu) were treated on 293T cells overexpressing Strep-AIMP2-DX2 and 293T cells not over-expressing, respectively for 12 hours, and MTT (Amresco) assay was performed. Each experiment was performed three times independently. Strep-AIMP2-DX2 was overexpressed in 293T cells, in which HSP70 expression was reduced using HSP70-specific si-RNA (si-HSP70), and MTT assay was performed. Each experiment was performed three times independently.

Figure 6A:
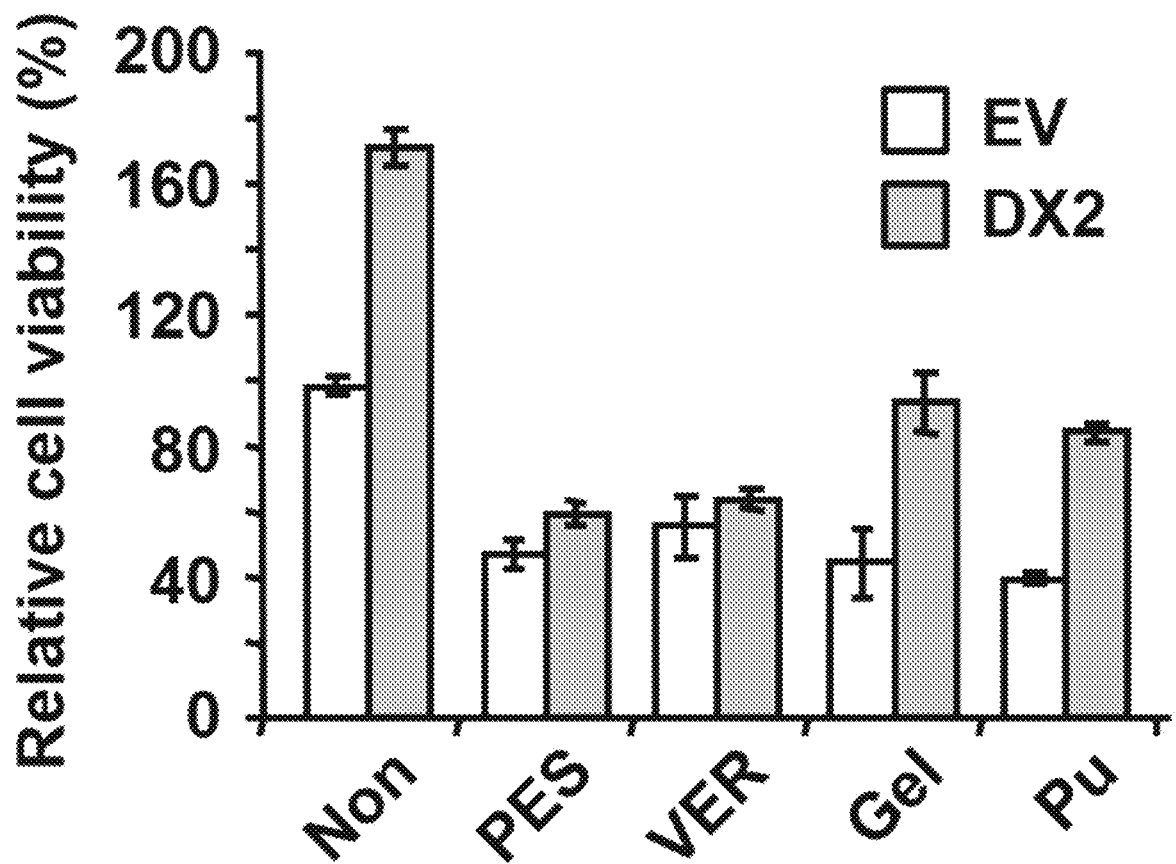
FIG. 6A shows the results of confirming whether cell growth is inhibited, when 293T cells overexpressing AIMP2-DX2 were treated with the HSP70 inhibitors PES (Pifithrin-u) and VER (VER155008) or with the HSP90 inhibitors Gel (Geldanamycin) and PU (PUH71).
Figure 6B:
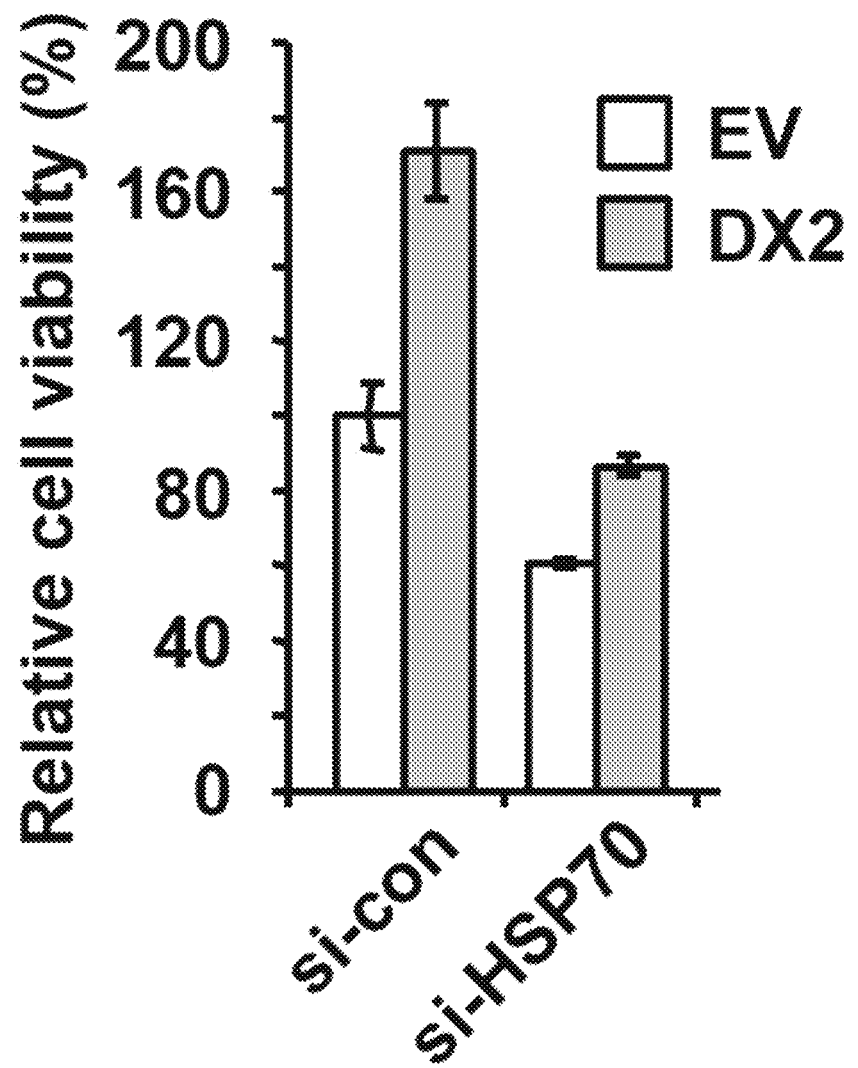
FIG. 6B shows the results of observing a cell growth in cells in which HSP70 expression was inhibited by si-HSP70.

The results are shown in FIGS. 6A and 6B.

As shown in FIG. 6A, after treatment with HSP70 inhibitors PES and VER, HSP90 inhibitors Gel and Pu, it was observed whether in a cell growth by AIMP2-DX2 increase. No increase in cell growth by AIMP2-DX2 was observed when the HSP70 inhibitor was treated. In addition, as shown in FIG. 6B, after the expression of HPS70 was reduced by the si-RNA technique, no cell growth was observed by AIMP2-DX2. These results indicate that HSP70 regulates cell growth through DX2.

Figure 6C:
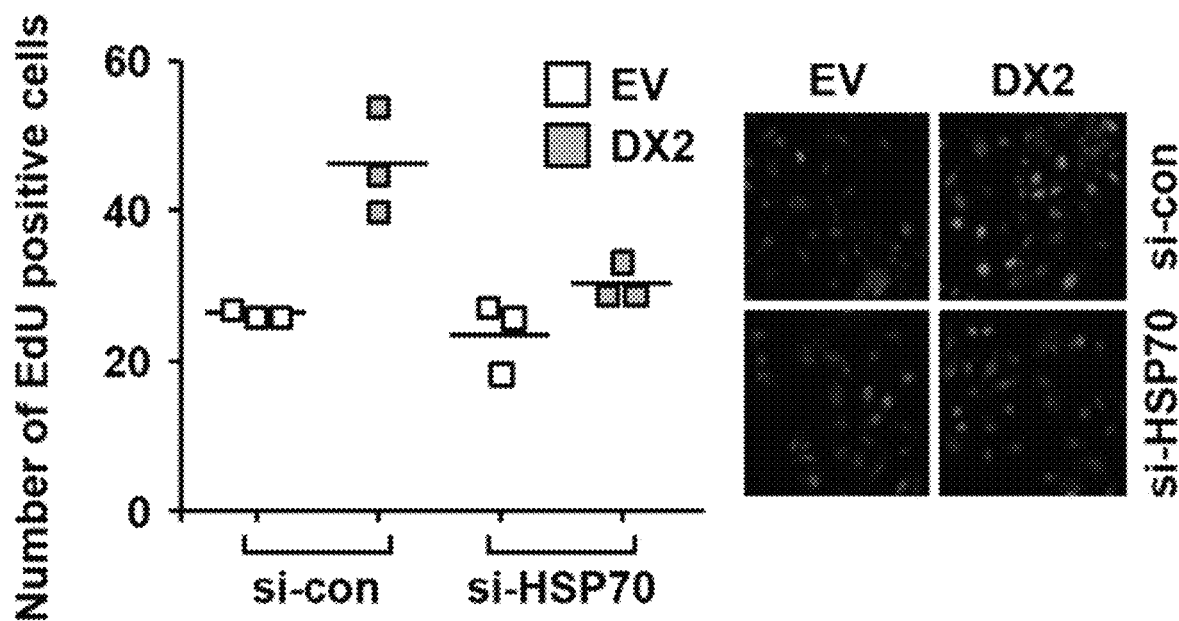
FIG. 6C shows the results of observation DNA synthesis as a result of cell growth by AIMP2-DX2 through the EdU assay, after the expression of HSP70 was reduced through si-RNA technique.

On the other hand, after the expression of HSP70 was reduced by the si-RNA technique, the DNA synthesis resulting from the cell growth by AIMP2-DX2 was observed through the EdU assay. As a result, when the expression of HSP70 is decreased, it can be seen that no increase in DNA synthesis through the expression of AIMP2-DX2 is observed (FIG. 6C).

Example 6: Detection of Binding Inhibitors of AIMP2-DX2 and HSP70

Figure 7A:
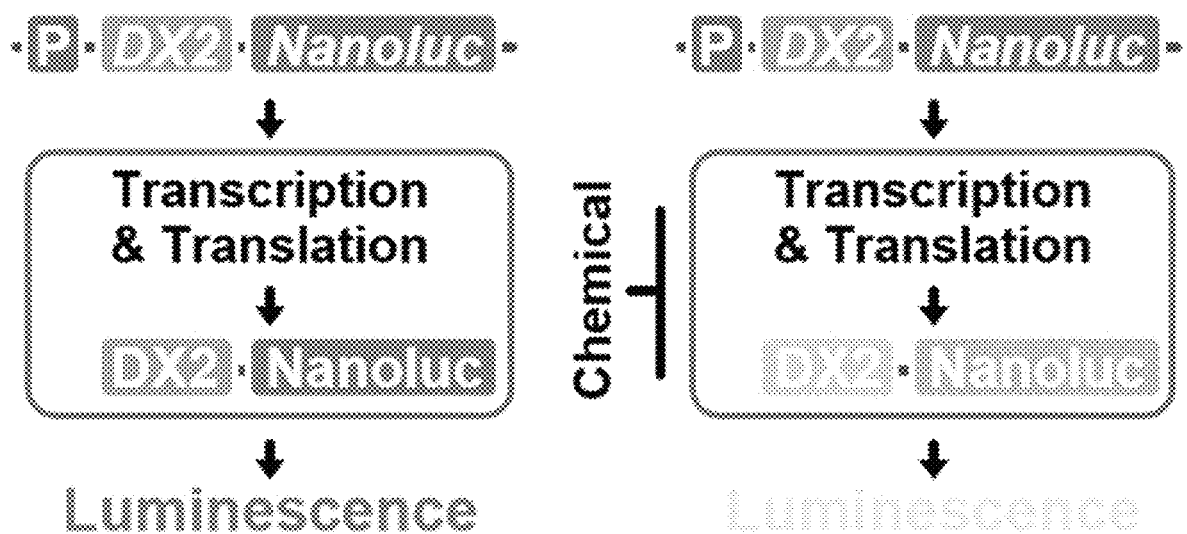
FIG. 7A is a schematic diagram of AIMP2-DX2 monitoring assay for searching for compounds that reduce AIMP2-DX2.

As shown in FIG. 7A, after making the AIMP2-DX2 monitoring assay, compounds that reduce AIMP2-DX2 were primarily selected by treating the compounds present in the compound library of the present inventors. Of the compounds that were primarily selected, a compound, which did not decrease AIMP2 and affected only cancer cells without affecting normal cells as measured by MTT assay for a cell viability, was finally selected.

Figure 7B:
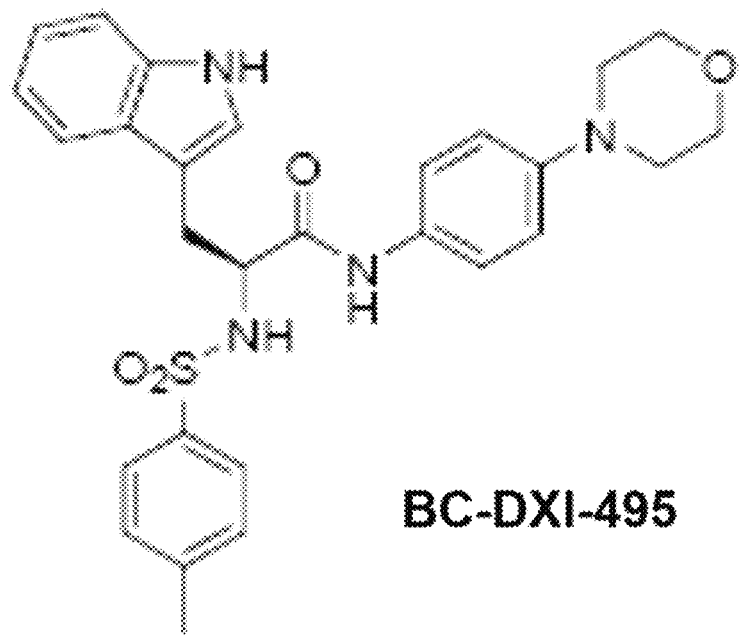
FIG. 7B is a diagram showing the formula of BC-DXI-495 compound which is a binding inhibitor of AIMP2-DX2 and HSP70 selected through AIMP2-DX2 monitoring assay.

The selected compound was named BC-DXI-495 and its structure is shown in FIG. 7B.

Example 7: Inhibition of BC-DXI-495 in Binding of AIMP2-DX2 and HSP70, and DX2 Expression It was evaluated whether or not BC-DXI-495 selected through Example 6 could inhibit the binding of AIMP2-DX2 and HSP70. After treatment of 293T cells overexpressing Strep-DX2 with the BC-DXI-495 compound for 12 hours at different concentrations (2.5, 5, 10 uM), the cells were lysed with PBS containing 1% of a reagent sold under the tradename TRITON™ X-100 (BD Science). After lysate was centrifuged at 13,200 rpm, the protein expression level of AIMP2-DX2 and AIMP2 was confirmed by western blot in the separated suspension and precipitate. Expression level of AIMP2-DX2 was confirmed using StrepMAB-Classic-HRP (IBA).

Figure 8A:
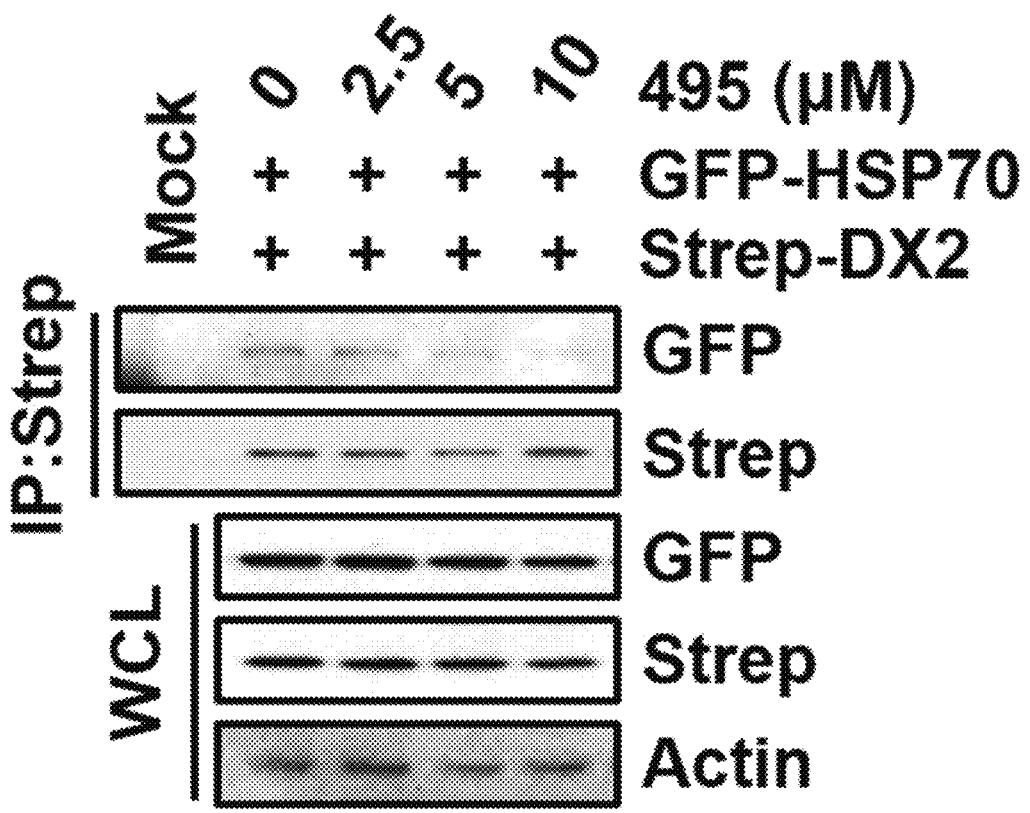
FIG. 8A shows the results of western blotting to confirm whether the binding of AIMP2-DX2 and HSP70 is inhibited by the treatment of BC-DXI-495 compound.

The results are shown in FIG. 8A.

As shown in FIG. 8A, when the BC-DXI-495 compound was treated in a concentration-dependent manner, it was confirmed that the binding of AIMP2-DX2 and HSP70 decreased in a concentration-dependent manner.

To confirm the reduction of AIMP2-DX2 and AIMP2 by the BC-DXI-495 compound, after A549 cells were overexpressed with nanoluciferase-AIMP2-DX2 and nanoluciferase-AIMP2, respectively, and treated with BC-DXI-495 compound in a concentration-dependent manner (2.5, 5, 10, 20, 40 uM) for 4 hours. After treatment, AIMP2-DX2 and AIMP2 protein level in the cells was confirmed by luciferase assay (cat #). The degree of luciferase inhibition at each concentration was measured, and the concentration of the compound leading to 50% reduction of AIMP2-DX2 and AIMP2 was calculated, which was expressed as IC50. In addition, the BC-DXI-495 compound was treated with H460 cells at different concentrations (2.5, 5, 10 uM) of 12 hours, and then AIMP2-DX2, AIMP2, and Actin protein expression and AIMP2-DX2, AIMP2 and Actin mRNA expression were observed by western blot and RT-PCR.

Figures 8B, 8C:
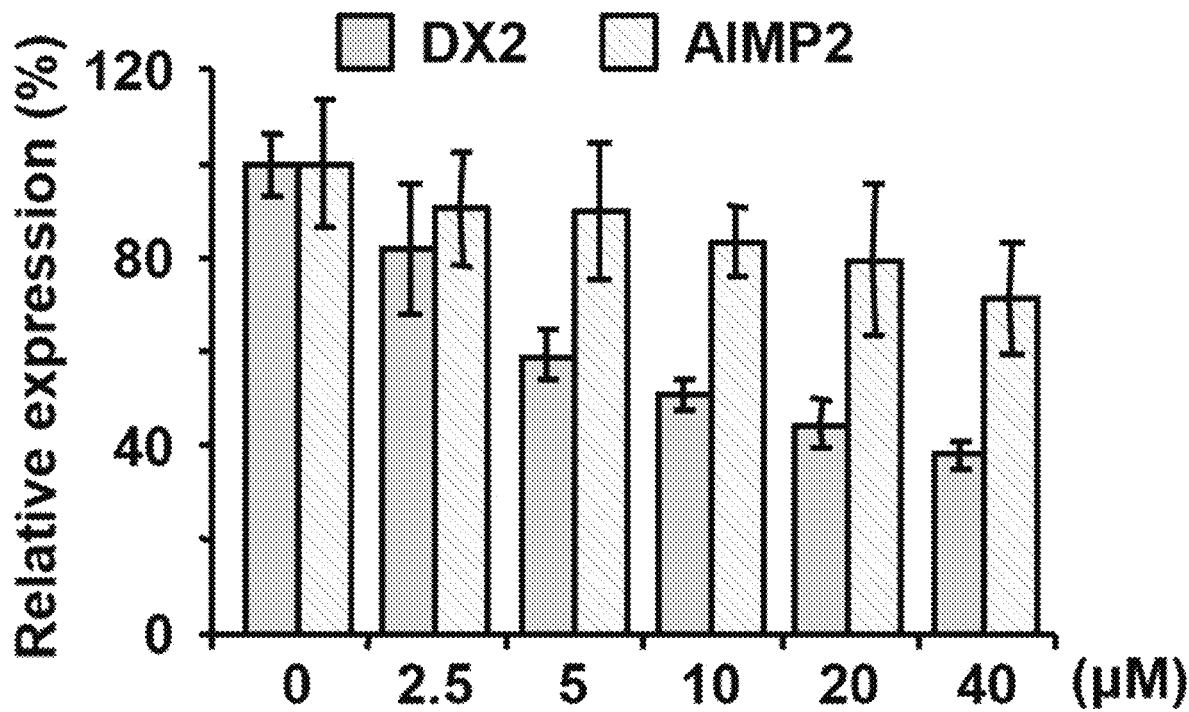
FIG. 8B shows the results of luciferase assay for the expression of AIMP2-DX2 or AIMP2 after treatment with BC-DXI-495 at various concentrations in cells overexpressing AIMP2-DX2 or AIMP2.
FIG. 8C shows the results of digitizing the results of FIG. 8B, and calculating the concentration (IC50) which inhibits the expression of each protein by 50%.
Figure 8D:
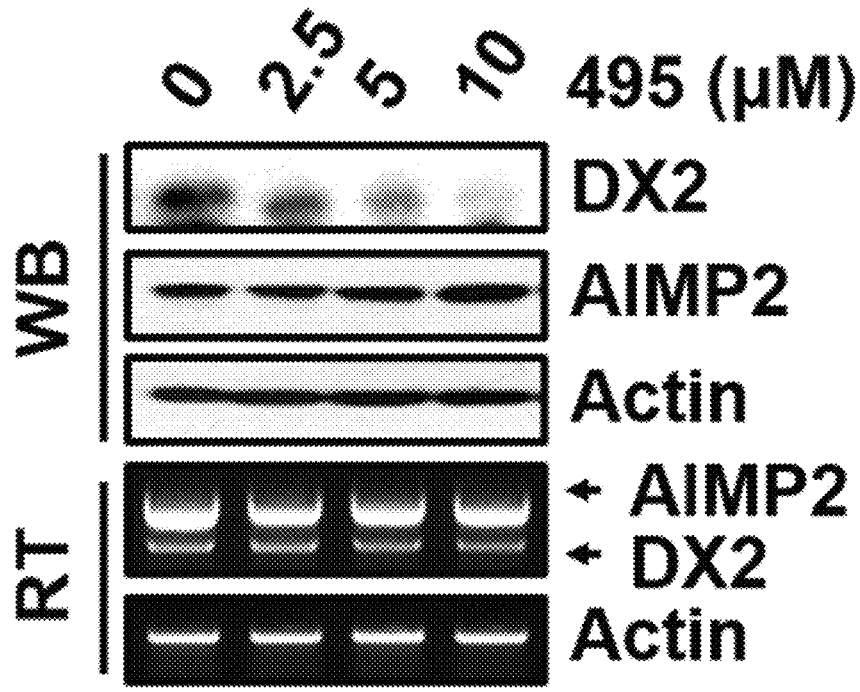
FIGS. 8D and 8E show the results of AIMP2-DX2, AIMP2 and Actin protein expression and AIMP2-DX2, AIMP2 and Actin mRNA expression by western blot and RT-PCR, respectively after H460 cells was treated with the BC-DXI-495 compound for 12 hours at a concentration (2.5, 5, 10 uM).
Figure 8E:
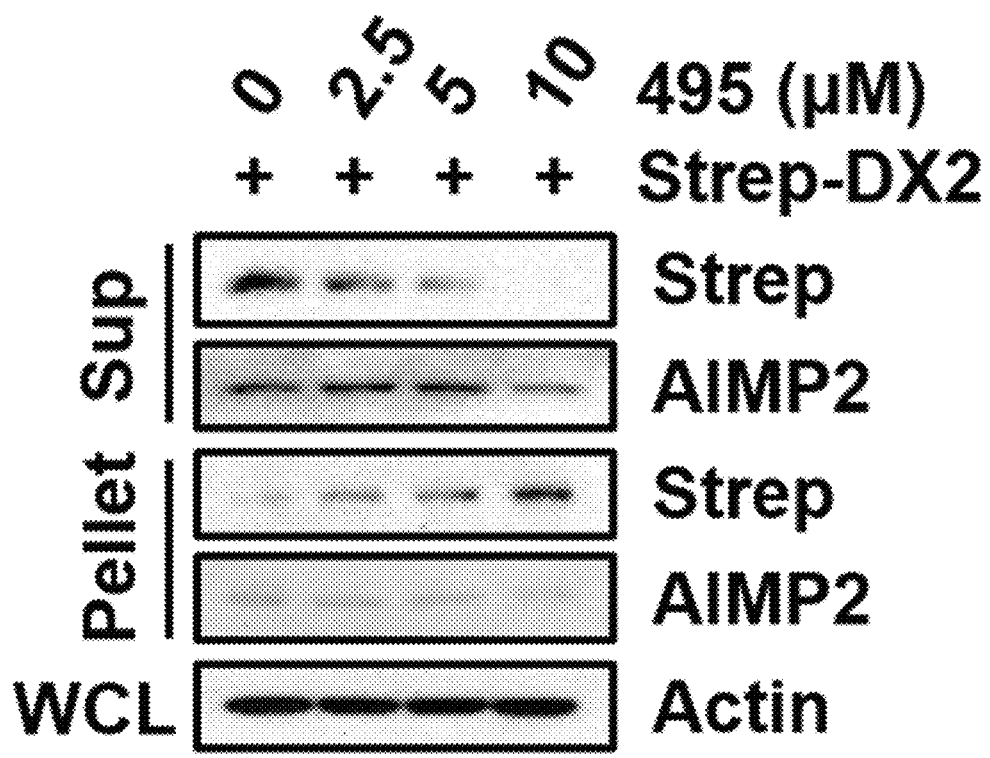

As a result, as shown in FIGS. 8B and 8C, it was confirmed that the BC-DXI -495 compound did not affect the expression of AIMP2 (IC50>100 uM), but specifically decreased AIMP2-DX2 expression (IC50: 4.2 uM). When the BC-DXI -495 compound is treated in a concentration-dependent manner, it was confirmed that AIMP2-DX2 protein specifically decreases without affecting AIMP2 (FIG. 8D). In addition, when the BC-DXI-495 compound was treated in a concentration-dependent manner, soluble AIMP2-DX2 protein (suspended layer fraction) decreased, whereas insoluble AIMP2-DX2 protein (precipitate fraction) increased (FIG. 8E).

Example 8: Evaluation of Anti-Cancer Efficacy of BC-DXI-495

8-1. Cytotoxicity of BC-DXI-495

In order to examine how the cell activity of lung cancer and normal lung cells was changed by the BC-DXI-495 compound, A549 (Lung cancer cells) and WI-26 (Normal lung cells) were treated with BC-DXI-495 in a concentration-dependent manner (2.5, 5, 10, 20, 40 uM). After treatment, MTT assay was performed to measure the activity of each cells. The concentration of the compound of causing 50% reduction of the cell activity was calculated, which was expressed as IC50

As shown in FIG. 9A, the BC-DXI-495 compound was treated in a concentration-dependent manner on lung cancer cell A549 and normal lung cell WI-26. As a result, it was found that only lung cancer cells induce apoptosis without any effect on normal cells.

In addition, doxycycline (0.5 mg/ml) was treated on A549, a lung cancer cell capable of inducing AIMP2-DX2 expression by Doxycycline (Sigma), and then cell growth was induced by AIMP2-DX2. Doxycycline was treated every 48 hours, and on Day 7, BC-DXI-495 (40 uM) was treated to observe its effect of inhibiting cell growth and inducing cell death for 96 hours.

As shown in FIG. 9B, it was found that the cytotoxicity by the BC-DXI-495 compound was induced greater upon inducing the expression of the AIMP2-DX2 protein (Pink graph) than otherwise.

In addition, the BC-DXI-495 compound was treated at different concentrations in two lung normal cells (WI-26, WI-38) and seven lung cancer cells (NCI-H2087, HCC-1359, HCC-95, HCC-366, HCC-1438, HCC-1588, NCI-H460) having different AIMP2-DX2 expression levels, and MTT assay was performed, GI50 was calculated. The AIMP2-DX2 expression level in each cell was confirmed by western blot.

As shown in FIG. 9C, the lung cancer cells were divided into 3 groups (Low, Median, High) according to the degree of endogenous AIMP2-DX2 protein expression, and the degree of cytotoxicity (GI50) was measured by treating with BC-DXI-495. As a result, it was found that the cell-death effect by the compound was excellent in cells having higher expression levels of AIMP2-DX2.

8-2. In Vivo Evaluation of Anti-Cancer Efficacy of BC-DXI-495

After 5×10$^6$ H460 cells were injected into the epidermis of 8-week-old Balb/c nude mice to form tumors, the BC-DXI-495 compound was injected 5 times a week at a concentration of 50 mg/kg for a total of 10 times, while taxol, a positive control, was injected twice a week at a concentration of 15 mg/kg for a total of 5 times. After the end of the experiment, the tumors were separated and weighed. The body weight and tumor size of the experimental animals were measured twice a week.

H460 cells with high AIMP2-DX2 expression were xenografted into mice, followed by the administration of the BC-DXI-495 compound at 50 mg/kg. It was found that the growth of cancer cells was inhibited to a degree similar to that of the control group Taxol (15 mpk). On the other hand, this tumor suppressive effect was also confirmed in the tumor weight (FIGS. 10A, 10B and 10C). There was no effect on the body weight of mice during the course of the experiment (FIG. 10D).

INDUSTRIAL APPLICABILITY

Based on the findings that HSP70 binds to and stabilizes directly with AIMP2-DX2, one of the major causative proteins of cancer, the present invention provides an anti-cancer agent screening method that selects a substance of reducing the binding level of AIMP2-DX2 and HSP70 as an anti-cancer agent by using an AIMP2-DX2 or a fragment thereof and HSP70 or a fragment thereof, and a composition for preventing or treating cancer comprising an anti-cancer agent selected by the screening method as an active ingredient. The selected substances according to the present invention such as siRNA and shRNA inhibiting the expression of HSP70 and a compound that inhibits the binding of HSP70 to AIMP2-DX2 are highly industrially useful because they are effective in lowering the level of AIMP2-DX2 protein in cancer and inhibiting the development and progression of cancer.

What is claimed is:

1. A method for screening an anti-cancer agent, the method comprising the steps of:
   (a) contacting AIMP2-DX2 or a fragment thereof with HSP70 or a fragment thereof in the presence or absence of a test substance;
   (b) measuring a binding level of AIMP2-DX2 or a fragment thereof with HSP70 or a fragment thereof in the presence or absence of the test substance;
   (c) comparing the binding level of AIMP2-DX2 or a fragment thereof with HSP70 or a fragment thereof in the presence of the test substance with the binding level of AIMP2-DX2 or a fragment thereof with HSP70 or a fragment thereof in the absence of the test substance to determine a change in the binding level of AIMP2-DX2 or a fragment thereof with HSP70 or a fragment thereof by the test substance;
   (d) selecting the test substance that reduces the binding level of AIMP2-DX2 or a fragment thereof with HSP70 or a fragment thereof; and
   (e) verifying an anti-cancer activity of the selected test substance in cells or animals, wherein the cancer is a cancer expressing AIMP2-DX2, wherein AIMP2-DX2 comprises the amino acid sequence of SEQ ID NO: 1 and the fragment of AIMP2-DX2 comprises amino acid residues 1 to 87 of SEQ ID NO: 1, wherein the fragment of AIMP2-DX2 has a binding affinity to HSP70, and wherein HSP70 comprises the amino acid sequence of SEQ ID NO: 3, and the fragment of HSP70 consists of amino acid residues 385 to 536 of SEQ ID NO: 3, wherein the fragment of HSP70 has a binding affinity to AIMP2-DX2.

2. The method of claim 1, wherein the method further comprises the following steps between the steps (d) and (e);
   (1) contacting the test substance with a cell expressing AIMP2-DX2;
   (2) measuring a protein level of AIMP2-DX2 in the cell and in a control cell with which the test substance is not contacted, respectively; and
   (3) selecting the test substance which reduces the protein level of AIMP2-DX2 in comparison with the control cell.

3. The method of claim 1, wherein the binding level in step (b) is measured by at least a method selected from the group consisting of a two-hybrid method, a co-immunoprecipitation assay, a co-localization assay, a scintillation proximity assay (SPA), an UV or chemical cross-linking method, mass spectrometry (MS), nuclear magnetic resonance (NMR), a fluorescence polarization assay (FPA) and an in vitro pull-down assay.

4. The method of claim 1, wherein the cancer is selected from the group consisting of breast cancer, lung cancer, colon cancer, anal cancer, astrocytoma, leukemia, lymphoma, head and neck cancer, liver cancer, testicular cancer, cervical cancer, sarcoma, hemangioma, esophageal cancer, eye cancer, larynx cancer, oral cancer, mesothelioma, myeloma, oral cavity cancer, rectal cancer, laryngopharyngeal cancer, bladder cancer, uterine cancer, ovarian cancer, prostate cancer, cancer of the large intestine, pancreatic cancer, kidney cancer, stomach cancer, skin cancer, basal cell carcinoma, melanoma, squamous cell carcinoma, oral squamous cell carcinoma, colorectal cancer, glioblastoma, endometrial cancer and malignant glioma.

5. The method of claim 1, wherein the anti-cancer agent is selected from the group consisting of siRNA, shRNA, miRNA, ribozyme, DNAzyme, peptide nucleic acid (PNA), antisense oligonucleotide, antibody, aptamer, peptide, natural extracts and chemical substance.

* * * * *

SEQUENCE LISTING

```
<160> NUMBER OF SEQ ID NOS: 6

<210> SEQ ID NO 1
<211> LENGTH: 251
<212> TYPE: PRT
<213> ORGANISM: Homo sapiens
<220> FEATURE:
<221> NAME/KEY: MISC_FEATURE
<222> LOCATION: (1)..(251)
<223> OTHER INFORMATION: Human AIMP2-DX2

<400> SEQUENCE: 1

Met Pro Met Tyr Gln Val Lys Pro Tyr His Gly Gly Gly Ala Pro Leu
1               5                   10                  15

Arg Val Glu Leu Pro Thr Cys Met Tyr Arg Leu Pro Asn Val His Gly
            20                  25                  30

Arg Ser Tyr Gly Pro Ala Pro Gly Ala Gly His Val Gln Asp Tyr Gly
        35                  40                  45

Ala Leu Lys Asp Ile Val Ile Asn Ala Asn Pro Ala Ser Pro Pro Leu
    50                  55                  60

Ser Leu Leu Val Leu His Arg Leu Leu Cys Glu His Phe Arg Val Leu
```

```
                65                  70                  75                  80
Ser Thr Val His Thr His Ser Ser Val Lys Ser Val Pro Glu Asn Leu
                    85                  90                  95

Leu Lys Cys Phe Gly Glu Gln Asn Lys Lys Gln Pro Arg Gln Asp Tyr
            100                 105                 110

Gln Leu Gly Phe Thr Leu Ile Trp Lys Asn Val Pro Lys Thr Gln Met
        115                 120                 125

Lys Phe Ser Ile Gln Thr Met Cys Pro Ile Gly Glu Gly Asn Ile
    130                 135                 140

Ala Arg Phe Leu Phe Ser Leu Phe Gly Gln Lys His Asn Ala Val Asn
145                 150                 155                 160

Ala Thr Leu Ile Asp Ser Trp Val Asp Ile Ala Ile Phe Gln Leu Lys
                165                 170                 175

Glu Gly Ser Ser Lys Glu Lys Ala Ala Val Phe Arg Ser Met Asn Ser
            180                 185                 190

Ala Leu Gly Lys Ser Pro Trp Leu Ala Gly Asn Glu Leu Thr Val Ala
        195                 200                 205

Asp Val Val Leu Trp Ser Val Leu Gln Gln Ile Gly Gly Cys Ser Val
    210                 215                 220

Thr Val Pro Ala Asn Val Gln Arg Trp Met Arg Ser Cys Glu Asn Leu
225                 230                 235                 240

Ala Pro Phe Asn Thr Ala Leu Lys Leu Leu Lys
                245                 250

<210> SEQ ID NO 2
<211> LENGTH: 87
<212> TYPE: PRT
<213> ORGANISM: Homo sapiens
<220> FEATURE:
<221> NAME/KEY: MISC_FEATURE
<222> LOCATION: (1)..(87)
<223> OTHER INFORMATION: Fragment of human AIMP2-DX2

<400> SEQUENCE: 2

Met Pro Met Tyr Gln Val Lys Pro Tyr His Gly Gly Gly Ala Pro Leu
1               5                   10                  15

Arg Val Glu Leu Pro Thr Cys Met Tyr Arg Leu Pro Asn Val His Gly
            20                  25                  30

Arg Ser Tyr Gly Pro Ala Pro Gly Ala Gly His Val Gln Asp Tyr Gly
        35                  40                  45

Ala Leu Lys Asp Ile Val Ile Asn Ala Asn Pro Ala Ser Pro Pro Leu
    50                  55                  60

Ser Leu Leu Val Leu His Arg Leu Leu Cys Glu His Phe Arg Val Leu
65                  70                  75                  80

Ser Thr Val His Thr His Ser
                85

<210> SEQ ID NO 3
<211> LENGTH: 641
<212> TYPE: PRT
<213> ORGANISM: Homo sapiens
<220> FEATURE:
<221> NAME/KEY: MISC_FEATURE
<222> LOCATION: (1)..(641)
<223> OTHER INFORMATION: Human HSP70

<400> SEQUENCE: 3

Met Ala Lys Ala Ala Ala Ile Gly Ile Asp Leu Gly Thr Thr Tyr Ser
1               5                   10                  15
```

```
Cys Val Gly Val Phe Gln His Gly Lys Val Glu Ile Ile Ala Asn Asp
             20                  25                  30

Gln Gly Asn Arg Thr Thr Pro Ser Tyr Val Ala Phe Thr Asp Thr Glu
         35                  40                  45

Arg Leu Ile Gly Asp Ala Ala Lys Asn Gln Val Ala Leu Asn Pro Gln
 50                  55                  60

Asn Thr Val Phe Asp Ala Lys Arg Leu Ile Gly Arg Lys Phe Gly Asp
 65                  70                  75                  80

Pro Val Val Gln Ser Asp Met Lys His Trp Pro Phe Gln Val Ile Asn
                 85                  90                  95

Asp Gly Asp Lys Pro Lys Val Gln Val Ser Tyr Lys Gly Glu Thr Lys
             100                 105                 110

Ala Phe Tyr Pro Glu Glu Ile Ser Ser Met Val Leu Thr Lys Met Lys
         115                 120                 125

Glu Ile Ala Glu Ala Tyr Leu Gly Tyr Pro Val Thr Asn Ala Val Ile
130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                 165                 170                 175

Thr Ala Ala Ala Ile Ala Tyr Gly Leu Asp Arg Thr Gly Lys Gly Glu
             180                 185                 190

Arg Asn Val Leu Ile Phe Asp Leu Gly Gly Gly Thr Phe Asp Val Ser
         195                 200                 205

Ile Leu Thr Ile Asp Asp Gly Ile Phe Glu Val Lys Ala Thr Ala Gly
210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                 245                 250                 255

Lys Arg Ala Val Arg Arg Leu Arg Thr Ala Cys Glu Arg Ala Lys Arg
             260                 265                 270

Thr Leu Ser Ser Ser Thr Gln Ala Ser Leu Glu Ile Asp Ser Leu Phe
         275                 280                 285

Glu Gly Ile Asp Phe Tyr Thr Ser Ile Thr Arg Ala Arg Phe Glu Glu
290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                 325                 330                 335

Val Gly Gly Ser Thr Arg Ile Pro Lys Val Gln Lys Leu Leu Gln Asp
             340                 345                 350

Phe Phe Asn Gly Arg Asp Leu Asn Lys Ser Ile Asn Pro Asp Glu Ala
         355                 360                 365

Val Ala Tyr Gly Ala Ala Val Gln Ala Ala Ile Leu Met Gly Asp Lys
370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                 405                 410                 415

Asn Ser Thr Ile Pro Thr Lys Gln Thr Gln Ile Phe Thr Thr Tyr Ser
             420                 425                 430
```

```
Asp Asn Gln Pro Gly Val Leu Ile Gln Val Tyr Glu Gly Glu Arg Ala
        435                 440                 445
Met Thr Lys Asp Asn Asn Leu Leu Gly Arg Phe Glu Leu Ser Gly Ile
450                 455                 460
Pro Pro Ala Pro Arg Gly Val Pro Gln Ile Glu Val Thr Phe Asp Ile
465                 470                 475                 480
Asp Ala Asn Gly Ile Leu Asn Val Thr Ala Thr Asp Lys Ser Thr Gly
                485                 490                 495
Lys Ala Asn Lys Ile Thr Ile Thr Asn Asp Lys Gly Arg Leu Ser Lys
                500                 505                 510
Glu Glu Ile Glu Arg Met Val Gln Glu Ala Lys Tyr Lys Ala Glu
        515                 520                 525
Asp Glu Val Gln Arg Glu Arg Val Ser Ala Lys Asn Ala Leu Glu Ser
530                 535                 540
Tyr Ala Phe Asn Met Lys Ser Ala Val Glu Asp Glu Gly Leu Lys Gly
545                 550                 555                 560
Lys Ile Ser Glu Ala Asp Lys Lys Lys Val Leu Asp Lys Cys Gln Glu
                565                 570                 575
Val Ile Ser Trp Leu Asp Ala Asn Thr Leu Ala Glu Lys Asp Glu Phe
                580                 585                 590
Glu His Lys Arg Lys Glu Leu Glu Gln Val Cys Asn Pro Ile Ile Ser
        595                 600                 605
Gly Leu Tyr Gln Gly Ala Gly Gly Pro Gly Pro Gly Gly Phe Gly Ala
610                 615                 620
Gln Gly Pro Lys Gly Gly Ser Gly Ser Gly Pro Thr Ile Glu Glu Val
625                 630                 635                 640
Asp

<210> SEQ ID NO 4
<211> LENGTH: 152
<212> TYPE: PRT
<213> ORGANISM: Homo sapiens
<220> FEATURE:
<221> NAME/KEY: MISC_FEATURE
<222> LOCATION: (1)..(152)
<223> OTHER INFORMATION: Fragment of human HSP70

<400> SEQUENCE: 4

Ser Glu Asn Val Gln Asp Leu Leu Leu Leu Asp Val Ala Pro Leu Ser
1               5                   10                  15
Leu Gly Leu Glu Thr Ala Gly Gly Val Met Thr Ala Leu Ile Lys Arg
                20                  25                  30
Asn Ser Thr Ile Pro Thr Lys Gln Thr Gln Ile Phe Thr Thr Tyr Ser
            35                  40                  45
Asp Asn Gln Pro Gly Val Leu Ile Gln Val Tyr Glu Gly Glu Arg Ala
        50                  55                  60
Met Thr Lys Asp Asn Asn Leu Leu Gly Arg Phe Glu Leu Ser Gly Ile
65                  70                  75                  80
Pro Pro Ala Pro Arg Gly Val Pro Gln Ile Glu Val Thr Phe Asp Ile
                85                  90                  95
Asp Ala Asn Gly Ile Leu Asn Val Thr Ala Thr Asp Lys Ser Thr Gly
                100                 105                 110
Lys Ala Asn Lys Ile Thr Ile Thr Asn Asp Lys Gly Arg Leu Ser Lys
                115                 120                 125
Glu Glu Ile Glu Arg Met Val Gln Glu Ala Lys Tyr Lys Ala Glu
        130                 135                 140
```

```
Asp Glu Val Gln Arg Glu Arg Val
145                 150

<210> SEQ ID NO 5
<211> LENGTH: 49
<212> TYPE: DNA
<213> ORGANISM: Artificial Sequence
<220> FEATURE:
<223> OTHER INFORMATION: Artificially synthesized HSP70 forward primer

<400> SEQUENCE: 5
gcgtaatacg actcactata gggagaatgc ccccagctac gtggccttc                49

<210> SEQ ID NO 6
<211> LENGTH: 49
<212> TYPE: DNA
<213> ORGANISM: Artificial Sequence
<220> FEATURE:
<223> OTHER INFORMATION: Artificially synthesized HSP70 reverse primer

<400> SEQUENCE: 6
gcgtaatacg actcactata gggagataaa gcttggcgtc gcgcagagc                49
```